United States Patent
John et al.

(10) Patent No.: US 9,315,676 B2
(45) Date of Patent: Apr. 19, 2016

(54) GREEN APPROACH IN METAL NANOPARTICLE-EMBEDDED ANTIMICROBIAL COATINGS FROM VEGETABLE OILS AND OIL-BASED MATERIALS

(71) Applicant: RESEARCH FOUNDATION OF THE CITY UNIVERSITY OF NEW YORK, New York, NY (US)

(72) Inventors: George John, Edison, NJ (US); Praveen Kumar Vemula, Cambridge, MA (US); Pulickel Ajayan, Houston, TX (US); Ashavani Kumar, Houston, TX (US)

(73) Assignee: RESEARCH FOUNDATION OF THE CITY UNIVERSITY OF NEW YORK, New York, NY (US)

(*) Notice: Subject to any disclaimer, the term of this patent is extended or adjusted under 35 U.S.C. 154(b) by 0 days.

(21) Appl. No.: 13/937,742

(22) Filed: Jul. 9, 2013

(65) Prior Publication Data
US 2014/0102331 A1  Apr. 17, 2014

Related U.S. Application Data

(62) Division of application No. 12/812,663, filed as application No. PCT/US2009/031120 on Jan. 15, 2009, now abandoned.

(60) Provisional application No. 61/011,214, filed on Jan. 15, 2008, provisional application No. 61/125,782, filed on Apr. 28, 2008.

(51) Int. Cl.
| | |
|---|---|
| *C09D 5/14* | (2006.01) |
| *A01N 25/12* | (2006.01) |
| *A01N 59/16* | (2006.01) |
| *A01P 1/00* | (2006.01) |
| *A01N 59/20* | (2006.01) |

(Continued)

(52) U.S. Cl.
CPC . *C09D 5/14* (2013.01); *A01N 59/16* (2013.01)

(58) Field of Classification Search
CPC ..... C09D 5/14; A01N 59/16; A01N 2300/00; A01N 25/10; A01N 25/24; A01N 25/34
USPC .............. 106/18, 16; 424/405, 485, 618, 649, 424/646, 654, 641, 630
See application file for complete search history.

(56) References Cited

U.S. PATENT DOCUMENTS

| | | | | |
|---|---|---|---|---|
| 4,036,650 | A * | 7/1977 | Hasegawa et al. | ............ 430/525 |
| 6,720,006 | B2 | 4/2004 | Hanke et al. | |
| 2010/0317883 | A1 * | 12/2010 | Ohashi | .................. A01N 59/16 556/114 |

FOREIGN PATENT DOCUMENTS

KR        200399051        10/2005

(Continued)

OTHER PUBLICATIONS

Alkyd resin: retrieved from internet: http://www.britannica.com/EBchecked/topic/15764/alkyd-resin. retrieved on Dec. 20, 2012.

(Continued)

*Primary Examiner* — Ernst V Arnold
*Assistant Examiner* — Hong Yu
(74) *Attorney, Agent, or Firm* — Hoffmann & Baron, LLP

(57) ABSTRACT

The present invention generally relates to a method of making nanoparticles and uses thereof. In particular, the invention relates to methods of making metal nanoparticles (MNPs). The invention also relates to antimicrobial uses of the nanoparticles.

7 Claims, 10 Drawing Sheets

(56) References Cited

FOREIGN PATENT DOCUMENTS

| RU | 2 195 473 C1 | 12/2002 |
| WO | 0078282 | 12/2000 |
| WO | WO 2008/072736 A1 * | 6/2008 |

OTHER PUBLICATIONS

Cytotoxic: retrieved from internet: http://en.wikipedia.org/wiki/Cytotoxicity. Retrieved on Dec. 31, 2012.
Antimicrobial: retrieved from internet: http://en.wikipedia.org/wiki/Antimicrobial. Retrieved on Dec. 31, 2012.

* cited by examiner

GREEN APPROACH IN METAL NANOPARTICLE-EMBEDDED ANTIMICROBIAL COATINGS FROM VEGETABLE OILS AND OIL-BASED MATERIALS

CROSS REFERENCE TO RELATED APPLICATIONS

This is a divisional application of U.S. Ser. No. 12/812,663 filed Mar. 11, 2011, pending, which is a U.S. National Phase application under 35 U.S.C. §371 of International Patent Application No. PCT/US2009/031120, filed Jan. 15, 2009, and claims the priority of U.S. Provisional Application Nos. 61/011,214, filed Jan. 15, 2008, and 61/125,782, filed Apr. 28, 2008, all of which are incorporated herein by reference in their entireties. The International Application published in English on Jul. 23, 2009 as WO 2009/091900 under PCT Article 21(2).

FIELD OF THE INVENTION

The present invention generally relates to a method of making nanoparticles and uses thereof. In particular, the invention relates to methods of making metal nanoparticles (MNPs). The invention also relates to antimicrobial uses of the nanoparticles.

BACKGROUND

Renewable resources, such as plants and crops, are inexhaustible and clean sources of materials that, when used in industrial processes, often produce by-products. Strategic utilization of such industrial by-products (i.e., biomonomers) as starting materials for generating value-added products and building blocks in chemistry will have broad impact in industrial economy as well as in sustainable development (Lichtenthaler 2002, Corma 2007, Goldemberg 2007). The efficient utilization of renewable resources is possible for developing novel monomers, polymers, chemicals, and soft nanomaterials (John, *Soft Matter* 2006, Vemula, *J. Am. Chem. Soc.* 2006, Vemula 2007, John 2001, John 2002, John 2004, John, *Angew. Chem. Int Ed.* 2006, Rostrup-Nielsen 2005, Pagliaro 2007, Biermann 2000). Polymers are among the most important products of the chemical industry and are used for versatile applications in everyday life. Employing agricultural/industrial by-products in polymer applications (for instance, the production of packaging, textiles and other functional materials) will be highly advantageous due to their properties of being renewable and biodegradable. Additionally, these biomonomers may be converted into valuable polymers or novel amphiphiles to produce soft nanomaterials.

A primary by-product of cashew nuts is cashew nut shell liquid (CNSL), which is extracted from the by-product shells of the cashew nut. One can synthesize free radically polymerizable monomers from cardanol (a compound derived from CNSL) by simple modifications and then polymerize them for use in coating applications (John 1992, John 1993).

In addition to CNSL oil, another polymerizable oil is vegetable oil. Common household oil paint, the oldest form of modern paints, uses a binder that is derived from vegetable oils obtained from linseed or soya bean. Alkyd paints are based on alkyd resins (vegetable-derived drying oils), which contain a variety of polyunsaturated fatty-acid chains, commonly linoleic and linolenic acid and their triglycerides (Daniel 1964, Metzger 2006, Bieleman 2000), which undergo free radical-mediated autoxidation during the curing/drying process (Black 1978, Reich 1969) (FIGS. 1a-c). The use of naturally generated free radicals enables one to generate valuable oil-based products.

Coatings can be used to decorate or protect surfaces of interest (Bohannon 2005, Crisp 2003, Klaus 1999). In general, several natural oils, drying oils in particular, are excellent coating materials, and when exposed to air, they form a tough scratch-free film as a result of the oxidative drying (lipid autoxidation) process that occurs through a widely accepted 'free radical' mechanism in the presence of atmospheric oxygen (Black 1978, Reich 1969) (FIG. 1c). In addition, literature reports suggest that free radicals are known to reduce metal salts to their uncharged MNPs (Zhang 2006, Okitsu 1997). Free radical-induced MNP synthesis is well studied (Zhang 2006, Okitsu 1997).

Several methods have been reported for the preparation of organic-inorganic hybrid materials; and most of the techniques used to incorporate metals into polymeric matrices involve either chemical reactions such as reduction (Aymonier 2002), mixing preformed metal nanoparticles with polymers (Liu 2005), or complicated physical techniques (Heilmann 2002), such as sputtering (Dowling 2003), plasma deposition (Jiang 2004), and layer-by-layer deposition (Dai 2002). All of these techniques add time, cost, multistep synthesis, and complexity to the overall process of fabricating metal-particle-doped materials.

Metal nanoparticles have attracted a great deal of attention because of their unusual optical and electronic properties (Colvin 1994) with potential application in the area of catalysis, (Hoffman 1992) electron microscopy markers, (Baschong 1990) gene therapy (Elghanian 1997) and sensors. (Shipway 1999) Recent interests focused towards developing new applications of nanoparticles having antifungal, antibacterial properties and can be used as coating materials or packaging materials. Attempts have been made to design such materials by embedding a antimicrobial agent in existing well known coating or packaging materials. Silver nanoparticles are known for its antibacterial properties have been used in fabrics, polymer for various applications. (Prashant 2005, Wang 1994, Chou 2005) Prashant et al. attached the silver nanoparticles on the surface of polyurethane foam and used it for water filter to avoid the bacterial contamination of surface water. (Prashant 2005) Wang et al prepared the antibacterial utltrathin film of titanium phosphate containing silver nanoparticles. (Wang 1994) Antibacterial cellulose acetate has also been made by incorporating silver nanoparticles in cellulose acetate based membrane. (Chou 2005)

Silver nanoparticles have also been used to incorporate coating materials to make antibacterial paints. In most of the approaches, either nanoparticles were synthesized separately and attached to different support, or silver ions were reduced in the presence of support using external reducing agent. Perhaps the same process can be used for the synthesis of nanoparticles and integrating them in coating materials for different application. Recently Willner and co-workers formed super lattice of citrate stabilized gold nanoparticles and cyclobis (paraquat p-phenylene) on the ammonium-functionalized indium tinoxide (ITO) surface using electrostatic interaction. (Shipway 1999) The Au nanoparticles in the super lattice provide a rough conductive array for the electrochemical sensing of the π-donor aromatic compound. Mirkin and co-workers used the optical properties of gold nanoparticles for the detection of DNA down to a concentration of 50 fM. (Taton 2000) Gold show catalytic activity for the oxidation of carbon monoxide at nanoscale at higher temperature (Haruta 1988). This catalytic activity is due to high surface free energy of nanoparticles, which makes them useful for protective gas masks and household room air fresheners etc. Gold particles have also been recognized as good catalyst for water gas shift reaction, propylene epoxidation, and benzene oxidation etc. (Bond 1999).

Much of the recent research focused on developing metal nanoparticles-based flat panel displays, radio frequency identification tags, sensors and other disposable electronics. Future technology demands the organic substrate based devices which can be fabricated entirely by printing to reduce the costs associated with lithography, vacuum processing and ultra clean room conditions. The main challenge is to use the low temperature conductor suitable for printing and inkjet printing technology compatible to fabricate at low temperature on low cost plastics. Metal nanoparticles have also been investigated for the electronic applications because of possibility of their use in printing circuits on plastic. (Huang 2003) The low resistance circuits were fabricated on plastic using alkanethiol protected metal nanoparticles dispersion as an ink at lower temperature.

Other than electronic application, the nanoparticles have also been used as a pigment in paints due to surface plasmon resonance in the visible region. More precisely, gold and silver nanoparticles have been known as an artistic ruby and yellow colorant for stained glass and fine glassware, due to their inherent surface plasmon absorption. The ruby red or yellow color of the stained glass is stable for hundreds of years. In contrary, the red color of organic dyes in traditional paints often fades away within several years due to the short lifetime of typical organic compounds. Nippon Paint has recently developed the technology for the use of paints for cars, based on a polymer-stabilized gold colloid. This paint appears black in shaded areas and red in illuminated areas, giving a dynamic effect as the vehicle is in motion due to varying light conditions. (Iwakoshi 2003) Use of this type of dynamic color effect could be envisaged for use in security devices, such as 'watermarking' of valuable or confidential documents, and biomedical testing kits. Titanium dioxide nanoparticles have been used in paints as a whitener as well as photo-active catalyst for hygiene or self cleaning application.

Another advantage of using metal nanoparticles in paints is their high reflectivity of infrared radiation. The heat-loss occurs in three ways: convection, conduction and radiation. Insulation is quite effective to reduce the heat loss due to convection and conduction however it have very little effect on heat loss due to radiation. Metal nanoparticles (Ag, Au, Al, Cu, Rh) have reflectivity of 98-99% in the infrared (IR) portion of the spectrum so paints containing metal nanoparticles will increase the reflection of radiant heat. Therefore use of such kind of paints inside of exterior will reduce heat loss by radiation. Current paints manufactured by ChemRex are claimed to reflect 30% of the radiant incident heat. The radiation of a room at 70° F. will peak at a wavelength of 10 microns, according to the black-body equation. Calculation, based on refractive indices of the particles and the paint, and a wavelength of 10 µm and particles size, shows that the reflectivity (scattering) increases linearly with the particle number density but not with the particle size.

Optical behavior of nanoparticles can be tuned by tailoring the shape of the particles. For example the optical absorption of gold nanoparticles can be tuned from visible region to near-infrared (NIR) region of electromagnetic spectrum by tailoring the shape of the particles from spherical to rod or triangular shape. The NIR absorption of the gold nanotriangles is expected to be having applications in hyperthermia of cancer cells and in IR-absorbing optical coatings. Sastry and co-workers showed that triangular gold nanoparticles coated glass films are highly efficient in absorbing IR radiation for potential architectural applications where the temperature in a compartment need to control due to expose of an infrared radiation. (Shankar 2005)

Most of the methods demand the synthesis of metal nanoparticles at large scale. Therefore it is most important to have a protocol for the synthesis of metal nanoparticles dispersion at large scale with precise control over the particles size and high metal concentration, yet most importantly keeping low production cost. Preparation of monolayer protected gold nanoparticles was achieved using the method previously documented by Brust et al. (Brust 1994) The key requirement for the scale-up of the nanoparticles was to reduce solvent levels used during the preparation stages. For example, it was reported that to prepare ca 0.25 g of the thiol-stabilized nanoparticle according to the Brust method would require ca 80 mL of toluene and 800 mL of ethanol for precipitation and purification. By extrapolation, 3 kg of product was reported to require 960 L of toluene and 10,000 L of ethanol. This was considered impractical for commercial production. With the described modifications, 0.5-1 kg quantities of gold chloride could be used to produce nanoparticles in 20 liter reaction vessels that were consistent in gold assay of the final product and also analytically similar for each batch. (Bishop 2002) The success of this technology is thought to be due to the low mobility of these nanoparticles during the early stages of heat treatment (50-150° C.) and also to their tendency to self-assemble and form 'loose' gold films before thermal decomposition of the stabilizing thiol ligand occurs.

Drying oils/alkyd resins are known as one of the oldest and the cheapest coatings materials and have attracted renewed interest because they are from renewable resources, like plant oils and independent of limited supply of petroleum-based products. Alkyd emulsions and high solid alkyd resins have shown a lot of success fulfilling the environmental demands. Moreover, life-cycle analysis of alkyd emulsion paints showed less effect on the environment than those based on acrylic dispersions. The possibility to obtain versatile, low cost, renewable, and low VOC emission products makes alkyd paints very attractive materials.

Silver and silver-based compounds are highly antimicrobial by virtue of their antiseptic properties to several kinds of bacterium, including *Escherichia coli* and *Staphylococcus aureus* (Sambhy 2006, Lansdown 2002, Kenawy 2007). Silver-based antimicrobial agents receive much attention because of the low toxicity of the active Ag ion to human cells (Williams 1989, Berger 1976), as well as it being a long-lasting biocide with high thermal stability and low volatility. However, although previous studies on silver and AgNPs have revealed some insights into the application of silver in several areas, little is known about the toxicity of AgNPs, where the size and surface area are recognized as important determinants for toxicity. AgNPs have been shown to possess good biocompatibility with mouse fibroblasts and human osteoblasts (Alt 2004), and their use for biological applications has been documented as well (Podsiadlo 2005). AgNPs are known to exhibit antibacterial properties and various research groups have investigated the mechanism of AgNP-mediated antibacterial activity (Morenes 2005, Gogoi 2006). As the size of the silver particles decreases down to the nanoscale regime, their antibacterial efficacy increases because of their larger total surface area per unit volume (Morenes 2005, Gogoi 2006).

One important aspect to consider is that although efficient antibacterial agents have been developed (Haldar 2006, Lewis 2005), they often fail to reach commercial needs owing to their complex, multi-step preparation methods and the high cost of production (Bohannon 2005). If the aim is to develop a general, simple (for example, single-step) procedure to make a solid surface bactericidal, then covalent attachment of polymers is probably not a viable option given the paucity of derivatization-amenable functional groups on most common surfaces.

Typically, nanoparticle synthesis involves external reducing agents and toxic organic solvents, which pose potential environmental and biological risks. Except for a few reports (Naik 2002, Raveendran 2003), it is difficult to find fully environmentally friendly methods for MNP synthesis.

Polymer-stabilized MNP composites (Morones 2007, Abyaneh 2007) are known to exhibit enhanced physicochemical stability, electrical and optoelectronic properties (Daniel 2004, Shan 2005). These composites are prepared either by simple entrapment of gold and silver nanoparticles (AuNPs and AgNPs, respectively) in a pre-synthesized polymer. Typically, the polymers have a thiol or a thiolate end group and are allowed to self-assemble on the MNPs' surface. The self-assembly occurs as a result of the specific interaction of the sulfur end-group with the surface (Hotchkiss 2007, Liu 2007, Fustin 2006). Another approach to creation of MNPs involves the reduction of gold salts with sodium borohydride in the presence of thio (Zheng 2004, Shimmin 2004) or dithioester (Shan 2003) end functionalized polymers. The reaction yields hybrids with AuNPs within the polymer shell. Physical entrapment of MNPs, however, has obstacles. For example, physical entrapment often produces heterogeneous hybrid materials. Importantly, it requires separate synthesis and purification of NPs and external doping into polymers (a multi-step process).

Oxidative drying of polyunsaturated oils is well known. In general, several natural oils, drying oils in particular, are excellent coating materials, and when exposed to air, they form a tough scratch-free film as a result of the oxidative drying (lipid autoxidation) process that occurs through a widely accepted free radical mechanism in the presence of atmospheric oxygen.

The three main steps in the preparation of MNPs involve the choice of the solvent medium used for the synthesis, the selection of an environmentally benign reducing agent, and the selection of a non-toxic material for the stabilization of the MNPs (see Anastas 1998). Although there are several known reducing agents, the majority of processes reported so far use reducing agents such as sodium borohydride ($NaBH_4$) and hydrazine ($NH_2$—$NH_2$). All of these are highly reactive chemicals and raise potential environmental and biological risks. Another and perhaps the most important issue is the choice of a capping agent to protect and passivate the nanoparticle surface, for better dispersion of MNPs.

Previously, novel organic-inorganic hybrid nanomaterials were prepared using self-assembled hydro/organogels (Vemula 2007, Vemula, *Chem. Commun.* 2006) and LCs as media for in situ synthesis of various MNPs (Zhang 2006, Okitsu 1997, Okitsu 1996).

In a prior art process, silver nanoparticles have been dispersed/incorporated in silicon rubber to achieve an antimicrobial effect, but in an amount less than cytotoxic silver concentration (U.S. Pat. No. 6,822,034). Silicon rubber is used in applications which include, for example, pan grips, camera eye caps, handles of bicycles, slipping preventative for spectacles, various rubber sheets and rubber coated cloth such as sheets and curtains that are used, for example in hospitals.

In another process, silver nanoparticles in organic matrix have also been used for antimicrobial activity for body care products (U.S. Pat. No. 6,720,006). A suspension containing silver nanoparticles with an individual size range of 5 to 50 nm was produced through thermal evaporation of silver into a liquid silicone oil base. Polypropylene granules are then co-extruded with this silicone oil using a Werner & Pfleiderer equipment to produce polypropylene granules containing up to 5% of the silver containing silicone oil. This master material was made into top sheets for diapers containing approximately 1000 ppm silver. The ELISA measurements demonstrated antibacterial efficacy.

Synthesis of nanoparticles (U.S. Pat. No. 6,974,493 and U.S. Pat. No. 6,929,675) in nonpolar medium is available. Harutyunyan, et al. (U.S. Pat. No. 6,974,493) synthesized the metal nanoparticles by heating or refluxing a mixture of two or more metal salts, such as metal acetates, and a passivating solvent, such as glycol ether, at a temperature above the melting point of the metal salts for an effective amount of time. Bunge, et al. (U.S. Pat. No. 6,929,675) followed different strategy which involves the thermal decomposition of organomettalic complexes of metal in organic phase. In this method, a solution of $(CU(C_6H_2(CH_3)_3)_5$, $(Ag(C_6H_2(CH_3)_3)_4$, or $(Au(C_6H_2(CH_3)_3)_5$ is dissolved in a coordinating solvent, such as a primary, secondary, or tertiary amine; primary, secondary, or tertiary phosphine, or alkyl thiol, to produce a mesityl precursor solution. This solution was decomposed by injecting it into an organic solvent heated to a temperature of approximately 100° C.

In yet another process, organically functionalized metal nanoparticles have been synthesized by mixing a metal precursor with an organic surface passivant and reacting the resulting mixture with a reducing agent to generate a free metal while binding the passivant to the surface of the free metal to produce organically functionalized metal particles (U.S. Pat. No. 6,103,868).

There is a need for a simpler, environmentally friendly process of preparing MNP-embedded materials. Accordingly, an objective of the present invention is the preparation of potent antibacterial coatings in a single step at ambient conditions without using external reagents or excessive energy for practical applications. Capitalizing on the versatility and reliability of oils (such as oil-based paints), the present invention uses an oxidative drying mechanism (lipid autoxidation) in the presence of metal salts to generate and stabilize MNPs (e.g., AgNPs) in oil, which competes, e.g., with previously implemented AgNP-based bactericidal agents (Morones 2005, Gogoi 2006). The process of the present invention thus provides an environmentally friendly method for making antimicrobial coatings containing metal nanoparticles.

SUMMARY OF THE INVENTION

The present invention relates to a successful, environmentally friendly process for synthesizing antimicrobial metal MNP-embedded materials, which can be performed in a single step. The naturally occurring oxidative drying process in oils, involving free radical exchange, is used as the fundamental mechanism for reducing metal salts and dispersing MNPs in an oil media (e.g., cashew nut shell liquid (CNSL) or vegetable oils), without the use of any external reducing or stabilizing agents. The well-dispersed MNP-in-oil dispersions can be used directly on nearly all kinds of surfaces such as wood, glass, steel, and various polymers. For example, surfaces coated with silver nanoparticle-in-oil dispersions prepared according to the present invention exhibit excellent antimicrobial properties. The present invention takes advantage of free radicals created during an oxidative drying process of oils to reduce metal salts, thereby creating a dispersion of metal nanoparticles throughout the oils.

The present invention is particularly useful for preparing antimicrobial coatings, decorative coatings, and antibacterial coatings in common places like hospitals, public places, restaurants, etc. The process of the present invention may also be used to prepare antimicrobial topical oils and antimicrobial soaps (for hand washing or general washing), and materials useful in linoleum floorings, building materials, glass coatings for UV/IR reductions, and antistatic coatings.

In particular, the nanoparticles of the invention are suitable for use in coating materials for hospital countertops, beds, and general medical equipment. The nanomaterials are also suitable for incorporation into flooring materials, such as vinyl flooring, linoleum flooring, etc. The nanoparticles of the invention have especially good antimicrobial activity against Methicillin-resistant *Staphyloccus Aureus* (MRSA) bacteria (also known as a super-bug), which are a serious problem in the healthcare industry. In general, antimicrobial compositions of the present invention would be beneficial when used in any public places where it is desirable to prevent MRSA infections.

The preparation of MNPs without using external reagents and in a single step (e.g., in situ) by excluding extra purification processes or transfer protocols has significant advantages over current methods. To overcome the above-mentioned hurdles, the present invention uses efficient supramolecular organic soft materials as hosts for the synthesis and stabilization of inorganic MNPs (Mallia 2007, Vemula 2007, Vemula, *Chem Commun.* 2006). The present invention also includes the use of a naturally occurring autoxidation/drying process in vegetable-based drying oils as a tool to prepare MNPs.

In one embodiment, the present invention relates to a method of preparing metal nanoparticle-embedded antimicrobial coatings from CNSL (i.e., cardanol, alkyd resins, urushiol, or other polyunsaturated oils/acids) using either naturally occurring or catalytic autoxidation or an oxidative drying process. Additionally, this method takes advantage of free radicals generated during the process of drying oils and oil-based materials (e.g., drying oils/alkyd paints) to reduce metal salts and create a dispersion of MNPs in an oil or oil-based material—e.g., silver- and gold-nanoparticle (AgNP- and AuNP-) embedded paints (in situ). AgNP-embedded oils (e.g., vegetable oils) and oil-based materials are particularly preferred due to their potential bactericidal activity.

In another embodiment, the invention relates to the synthesis and stabilization of AuNPs and AgNPs in a bio-based cardanyl acrylate polymer. During the drying process, naturally occurring cross-linking (autoxidation) of unsaturated alkyl chains is used as a tool to reduce metal salts and bind the nanoparticles. Since the nanoparticles are generated in situ, the use of external hazardous reducing agents is avoided.

In another embodiment, the present invention relates to a process for direct synthesis of nanoparticles into drying oil/alkyds/alkyd modified resins. Drying oil is a kind of vegetable oil, which dries at ambient conditions to form glossy films, and has been practiced for centuries in oil paintings, art materials and alkyd resins and coatings. The nanoparticles were formed by dissolving a salt in an oil medium and shaking. The stability and shelf life of nanoparticles is comparable to nanoparticles synthesized using a conventional process because of the passivation with polymer formed during the reaction. Nanoparticles exhibit prominent features in the UV-visible region of the electromagnetic spectrum due to the electronic transitions. This dispersion is useful for various applications such as novel chemical reactions on nanoscale curved surface and self-assembly of surface modified nanoparticles. Metal nanoparticle dispersions could also find applications in conducting coatings, fluorescent dispersions, antistatic and antimicrobial coatings. These metal nanoparticle-containing vegetable oils can be used as a colored coating on various substrate. More precisely, gold nanoparticles can be used as an artistic ruby colorant for stained glass and fine glassware, due to their inherent surface plasmon absorption. Hence, the present invention may be used for graceful, yet stable, colored glass, ceramics or any surfaces by using gold nanoparticles doped paints as thin films on these materials. There are a few hurdles that are avoided by using the process of the present invention. For instance, because the process of the present invention does not use an external reducing agent and stabilizing agent, further purification processing is not necessary; and coagulation of gold nanoparticles at higher concentrations is avoided as well.

The present invention relates to an antimicrobial composition that has a homogenous mixture of a drying oil and metallic nanoparticles with a particle size of 1 to 50 nm, where the composition is effective as an antimicrobial. Suitable drying oils include, for example, cashew nut shell liquid, linoleic acid, poppy oil, soyabean oil, urushi oil, linseed oil, sunflower oil, tung oil, alkyd resins, other vegetable oils, and combinations thereof. Suitable metallic nanoparticles include, for example, those with a metal such as silver, gold, nickel, platinum, palladium, cadmium, zinc, copper, and combinations thereof.

The metal nanoparticles are present in an amount that is antimicrobially effective, but less than a cytotoxic silver concentration. The nanoparticles are preferably present in an amount ranging from more than 1 nmol/L to less than 1 μmol/L. In the present invention, the metallic nanoparticles are dispersed in the drying oil and are present in an amount of 1 to 2,000 ppm, more preferably 5 to 1,000 ppm, and most preferably 10 to 250 ppm.

The present invention also relates to a method for preparing metal nanoparticles in a drying oil, comprising the steps of: (a) mixing a solution comprising metal ions with a solution comprising a drying oil in the presence of an organic solvent or an organometallic compound; (b) agitating the mixture for a period of 12 to 24 hours; and (c) polymerizing the drying oil by autoxidation to form metal nanoparticles in a polymerized oil.

The metal nanoparticles may be hydrophobic. Suitable metal ions include, for example, gold, silver, nickel, platinum, palladium, cadmium, zinc, copper, and combinations thereof. Suitable drying oils include, for example, cashew nut shell liquid, linoleic acid, poppy oil, soyabean oil, urushi oil, linseed oil, sunflower oil, tung oil, alkyd resins, and combinations thereof. Suitable organic solvents include, for example, n-hexane, chloroform, heptane, octane, petroleum ether, benzene, toluene, turpentine, and combinations thereof. Suitable organometallic compounds include, for example, silver benzoate, metal acetyl acetonates, metal carbonyls, nonpolar metal salts, iron acetyl acetonate, platinum acetyl acetonate, nickel acetyl acetonate, cobalt acetyl acetonate, cobalt acetate, iron petacarbonyl, and combinations thereof.

DETAILED DESCRIPTION OF THE INVENTION

The present invention relates to a process for an environmentally friendly process for preparing antimicrobial MNP-embedded materials in a single step, which utilizes an oxidative drying step in the presence of a metal salt. The naturally occurring oxidative drying process in oils, involving free radical exchange, is used as the fundamental mechanism for reducing metal salts and dispersing MNPs in the oil media, without the use of any external reducing or stabilizing agents. Acrylates and polyurethanes derived from CNSL, for example, can be used as starting materials for oxidative drying induced nanoparticle formation according to the present invention.

In the process of the present invention, no solvents are required for the synthesis of MNPs. Instead, the commercially available environmentally benign drying oils are used. Additionally, regarding the reducing agent, free radicals naturally generated in situ during the drying process of the present invention are used as reducing agents. This process does not require heating, and moreover the system is mild, renewable, cheap and non-toxic in nature. Regarding the choice of a capping agent to protect and passivate the nanoparticle surface for better dispersion of MNPs, the present invention uses the polymer (e.g., alkyd) resin itself acts as the protecting agent. Fatty acids and in situ-generated aldehydes and other intermediates act as stabilizing agents for MNPs.

Figure 5:
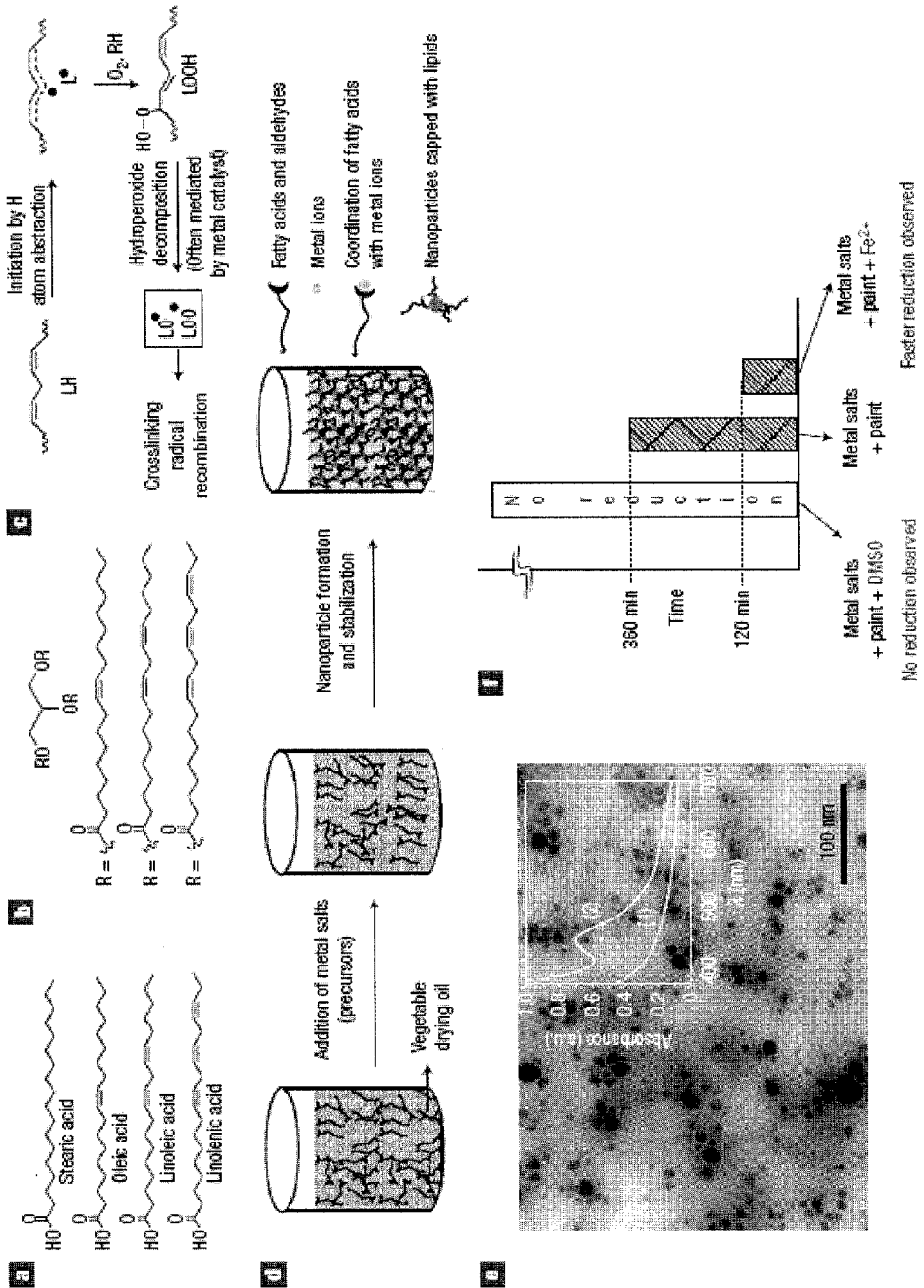
FIG. 5. Chemical structures of common fatty acids in drying oils, and synthesis and characterization of AgNPs in alkyd resins; (5a) chemical structures of fatty acids with different degrees of unsaturation that are present in alkyd resins; (5b) structures of general triglycerides present in alkyd resins; (5c) general mechanism for the free radical-mediated autoxidation process in drying oils; (5d) schematic diagram of in situ synthesis and stabilization of MNPs in drying oils; (5e) transmission electron micrograph of AgNPs synthesized in drying oils with an average size of 12-16 nm. The inset shows the absorption spectra of AgNPs with a surface plasmon resonance band; spectra were recorded at (1) 5 min and (2) 24 h after the addition of silver benzoate to the oils; and (5f) kinetics of the metal salt reduction process, time required for nanoparticle synthesis is plotted; the addition of a catalyst ($Fe^{2+}$) enhanced the generation of free radicals, which increased the rate of nanoparticle synthesis; in contrast, the addition of DMSO, which is a well-known free radical scavenger, completely prevented nanoparticle synthesis.

The presence of several in situ-generated free radicals such as LOO., LO. and L. (L=lipid chain) during autoxidation of drying oils is useful for the reduction of metal salts to synthesize MNPs in situ (FIG. 5c). For example, when silver benzoate was used as the precursor for MNPs in drying oil and the conventional ambient drying process was used, visual changes were observed. The oil phase became light yellow in color with time, which indicated the formation of AgNPs.

The process of the present invention was also tested with other metal salts—e.g., chloroauric acid ($HAuCl_4$) for an AuNP preparation. Appropriate choice of the organometallic salts facilitates the solubility of nanoparticle precursors into the oil medium. Silver salts, for example, undergo ligand exchange with fatty acids, causing the metal ions to dissolve in the oil and subsequent reduction by the free radicals to form nanoparticles (Zhang 2006, Okitsu 1997) (FIG. 5d).

Silver benzoate may be used as a starting material for preparing AgNPs, and chloroauric acid ($HAuCl_4$) may be used as a starting material for preparing for AuNPs to synthesize MNP-embedded polymers. The presence of several in situ generated free radicals, such as LOO., LO., and L. (L=cardanyl lipid chain), during the autoxidation of PCA could be well utilized for the reduction of metal salts to synthesize MNPs in situ.

In another embodiment, the present invention involves a process for the preparation of coating materials containing nanoparticles by a simple shaking process. This process involves dissolution of organometallic complex in oil medium and then in situ formation of nanoparticles in the organic phase due to drying of oil into polymeric matrix. The critical goal of the present invention is to provide an improved simple process for the nanoparticles based coating/flooring materials with antimicrobial (e.g., antibacterial) activity.

As used herein, the term "antimicrobial" refers to a product that is capable of destroying or inhibiting the growth of one or more microorganisms, including bacteria, protozoa, and viruses, preferably to an undetectable level.

Figure 9:
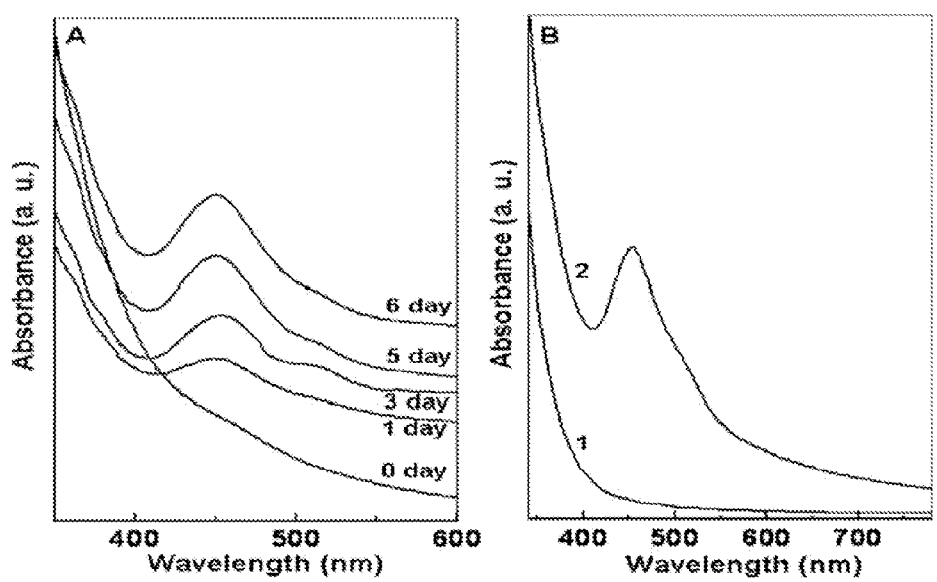
FIG. 9. (9a) UV-Visible spectra of silver benzoate in oil as a function of time. (9b) UV-visible spectra of Ag-oil (curve 2) and pure oil (curve 1) on the glass substrate.

This nanoparticles synthesis process was also simplified and silver compounds (e.g., silver nitrate, silver benzoate, etc.) were used as a precursor for the synthesis of silver nanoparticles directly from oil. In this process, the nanoparticle precursor was dissolved directly in oil phase, which upon reduction during drying process of oil generates nanoparticles. FIG. 9 is the UV-visible spectra of solution of silver salts in oil phase as a function of time.

One embodiment of the present invention relates to the use of a drying oil which mediates the formation of nanoparticles. This could be any kind of vegetable drying oils including alkyd resins and alkyd modified resins and paints. For example, linoleic acid, poppy oil, tung oil, other plant exudates such as urushi and cashew nutshell liquid may be used In another embodiment, the present invention is not limited to metal salts, and any other kind of organomaterial compound may be used, such as the class of metal acetyl acetonates (e.g., copper acetyl acetonate, iron actyl acetonate nickel acetyl acetonate, copper acetyl acetonate), class of metal carbonyls (e.g., iron pentacarbonyl, platinum acetyl acetonate, silver benzoate, silver nitrate, etc.

Another important embodiment of the present invention is this process can be performed using various organic solvents with different polarities such as n-hexane, chloroform, heptane, octane, petroleum ether, benzene, toluene and turpentine. Especially this is a key result when it comes to the commercial use of the nanoparticles, this process would help us to generate and store metal nanoparticles in several organic solvents and can be fulfilled the needs of the customers who often demands supply of metal nanoparticles in various solvents for specific applications and requirements.

EXAMPLES

The present invention is next described by means of the following examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Example 1

Figure 6:
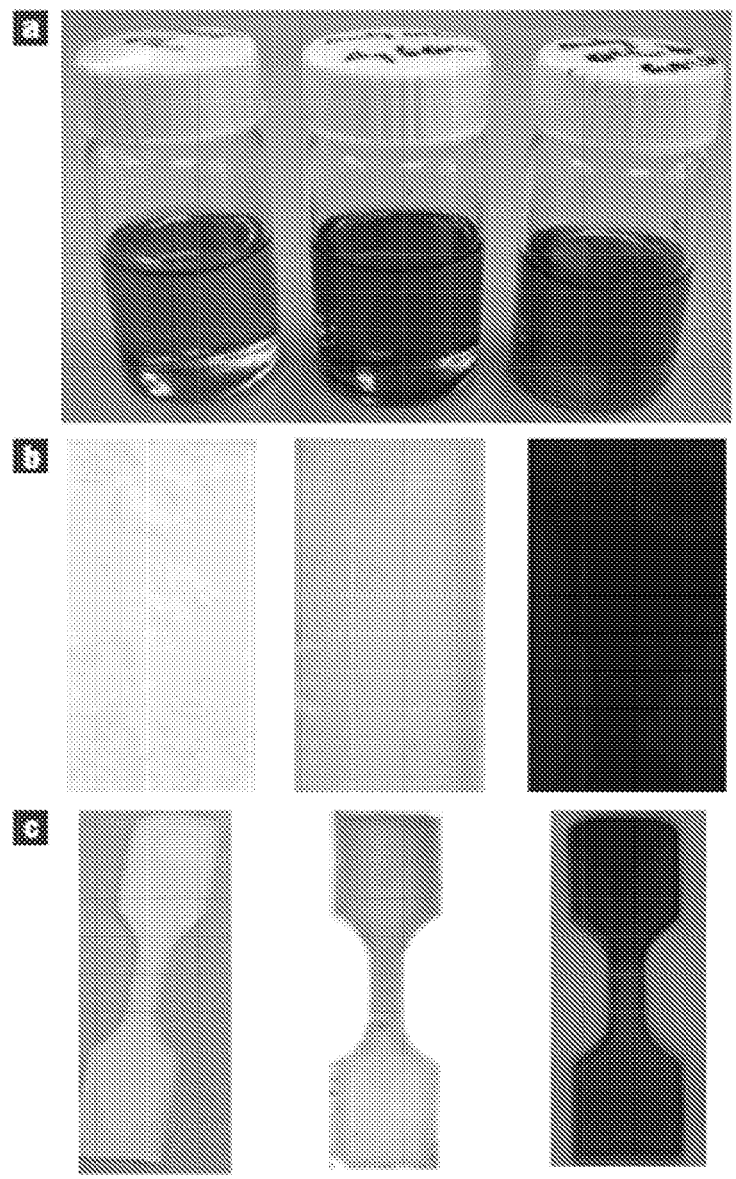
FIG. 6. Images of metal-salt-containing drying oils, and nanoparticle-embedded paint coatings. (6a) images of plain commercially available drying oil, and silver benzoate and chloroauric acid dissolved in drying oils (left to right); (6b) images of paint coatings without nanoparticles (left panels), AgNPs (middle panels) and AuNPs (right panels) on glass (b) surfaces; and (6c) images of paint coatings without nanoparticles (left panels), AgNPs (middle panels) and AuNPs (right panels) on polymer surfaces.

To investigate nanoparticle synthesis on surfaces, various surfaces such as glass, polypropylene, and poly(methyl methacrylate) were coated with metal ion-containing drying oils (e.g., oil-based paints) (FIG. 6). After about 6 hours of drying at ambient conditions, gold paint turned pink in color and silver paints turned slightly brownish yellow, indicating the formation of AuNPs and AgNPs in the coatings, respectively. It is likely that free radicals generated in situ during the autoxidation are responsible for the reduction of metal salts to generate nanoparticles.

The presence of AgNPs and AuNPs was confirmed by spectroscopic (ultraviolet-visible) and transmission microscopic techniques. The stability and shelf life of nanoparticles synthesized in drying oils are comparable or even better than those of nanoparticles synthesized using conventional processes (for example, sodium borohydride, citric acid and so on). The higher stability of the nanoparticles is due to the stabilization of the nanoparticles by the polymer matrix formed during the autoxidation. The stability of the nanoparticle film was confirmed by heating the nanoparticle-oil film at ambient conditions and was quite stable up to 200° C. for an hour without significant aggregation.

Figure 1:
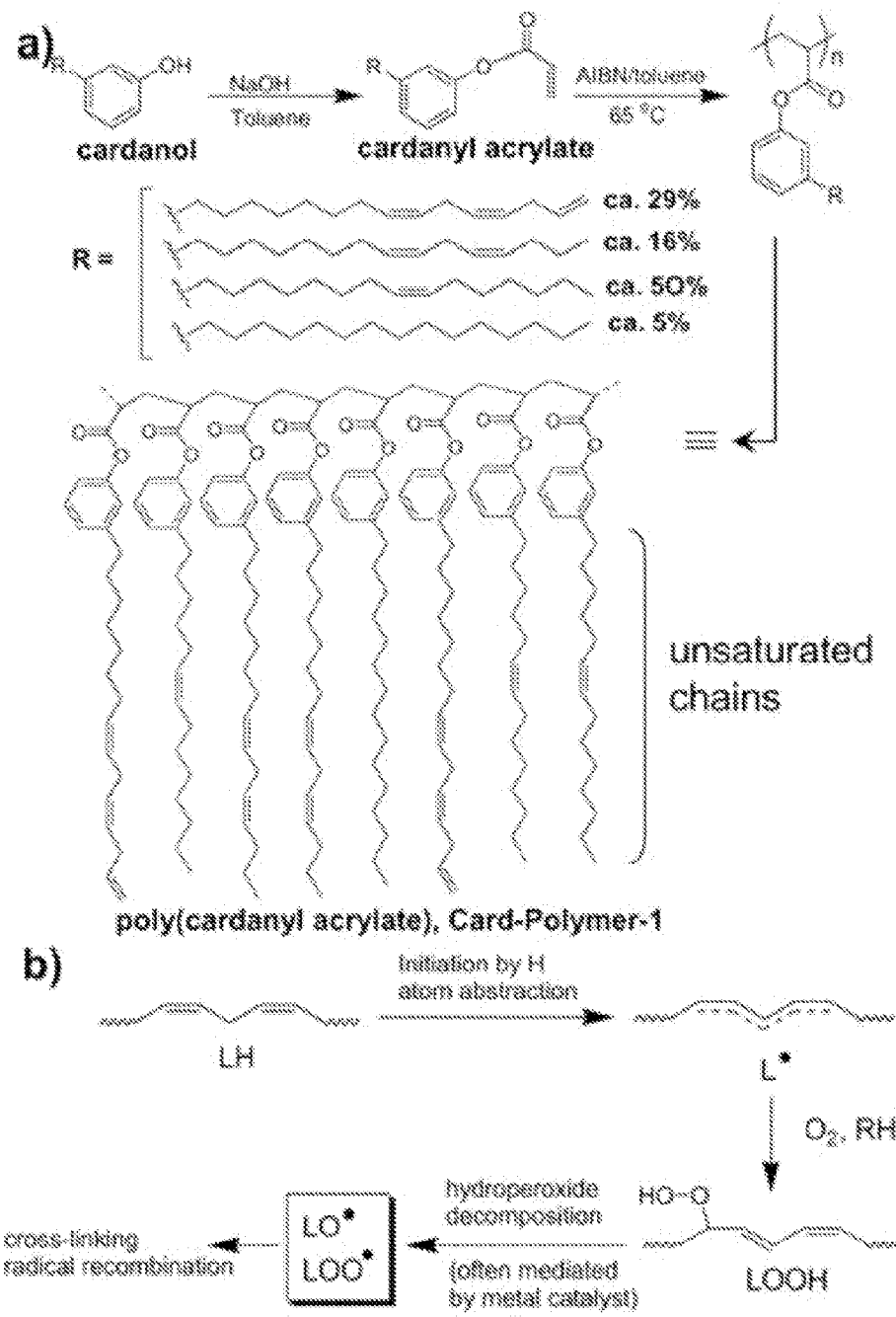
FIG. 1. (1*a*): Chemical structures and synthetic scheme of poly(cardanyl acrylate) (PCA). (1*b*) general mechanism for free radical mediated cross-linking of cardanyl polymer side chains.

The preparation of a synthetic polymer system and exploration of the metal salt reduction to generate MNPs within the polymer gives further insight into the mechanism of autoxidation of unsaturated alkyl chains that produce free radicals to reduce metal salts. Cardanol (obtained from thermal treatment of CNSL) exists as a mixture of four components differing in the degree of unsaturation in the side chain: 5% of 3-(pentadecyl)-phenol, 49% of 3-(8Z-pentadecenyl)-phenol, 17% of 3-(8Z,11Z-pentadecadienyl)-phenol, and 29% of 3-(8Z,11Z,14Zpentadecatrienyl)-phenol (Tyman 1979) (FIG. 1a). Cardanyl acrylate (CA) was synthesized by procedures reported earlier (John 1992). Subsequently, solution polymerization was achieved using azobisisobutyronitrile (AIBN) in toluene to obtain PCA, as shown in FIG. 1a. The PCA was dissolved in chloroform and could easily be cast into a thin transparent and sticky film by a solution-casting technique.

Figure 7:
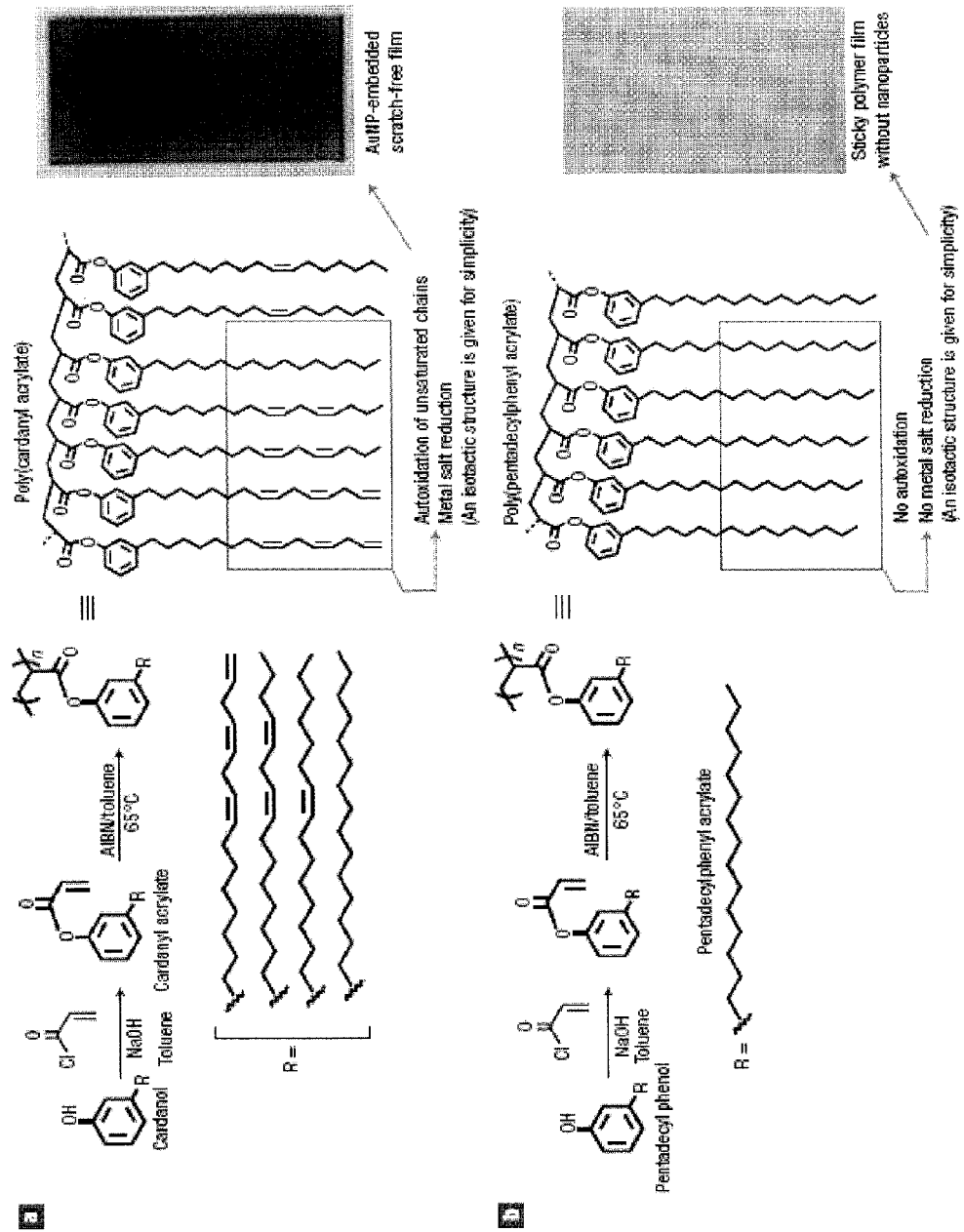
FIG. 7. AuNP synthesis in cardanol-based polymer films. (7a) synthesis of cardanyl acrylate and its polymerization to form PCA with a mixture of unsaturated alkyl chains, which was used for synthesis of AuNPs (the right image shows the AuNP-embedded polymer film); and (7b) synthesis of pentadecylphenyl acrylate (a saturated analogue), and its polymerization to produce a sticky transparent film that failed to show AuNP synthesis owing to the absence of the autoxidation process (the right image shows the sticky clear polymer film).

The resulting polymer has an acrylic backbone with many unsaturated alkyl side chains, which are easily amenable to the oxidative drying process, similar to the conventional drying oils (John 1992, John 1993). In previous studies, the oxidative drying (lipid autoxidation) process of poly(cardanyl acrylate) into crosslinked networks was demonstrated by various techniques (John 1992, John 1993). To prove the autoxidation-mediated metal salt reduction, poly(cardanyl acrylate) was dried in the presence of $HAuCl_4$, which produced a AuNP-embedded crosslinked polymer that was coated on a glass slide (FIG. 7a). As a control experiment, a polymer was synthesized with a saturated hydrocarbon chain, poly(pentadecylphenyl acrylate) (FIG. 7b). The saturated analogue failed to undergo oxidative drying (lipid autoxidation) owing to the absence of characteristic allylic unsaturation on the polymer side chains, which prevented nanoparticle synthesis. These results clearly support the hypothesis that the autoxidation process of unsaturated chains in drying oils is indeed responsible for the reduction of metal salts.

After heating to approximately 60° C. for about 30 minutes, or upon exposure to the air (ambient conditions) for 10 hours, the sticky film converted into non-sticky (scratch-free) transparent insoluble film. The cross-linking of PCA unsaturated hydrocarbon chains possibly occurred through the hydrogen insoluble polymer network (as shown in FIG. 1b). This was thoroughly characterized using various techniques such as infra-red spectroscopy, $^1$H-NMR and differential scanning calorimeter (John 1993). Cross-linking may have occurred through hydroperoxidation of allylic radical centers of cardanol alkyl chain, and during this process various free radicals were generated in situ (FIG. 1b). In the case of PCA, the side chains are brought close to each other by the acrylate polymer backbone and precisely aligned the allylic side chains for further cross-linking processes as shown schematically in FIG. 1a.

Figure 2:
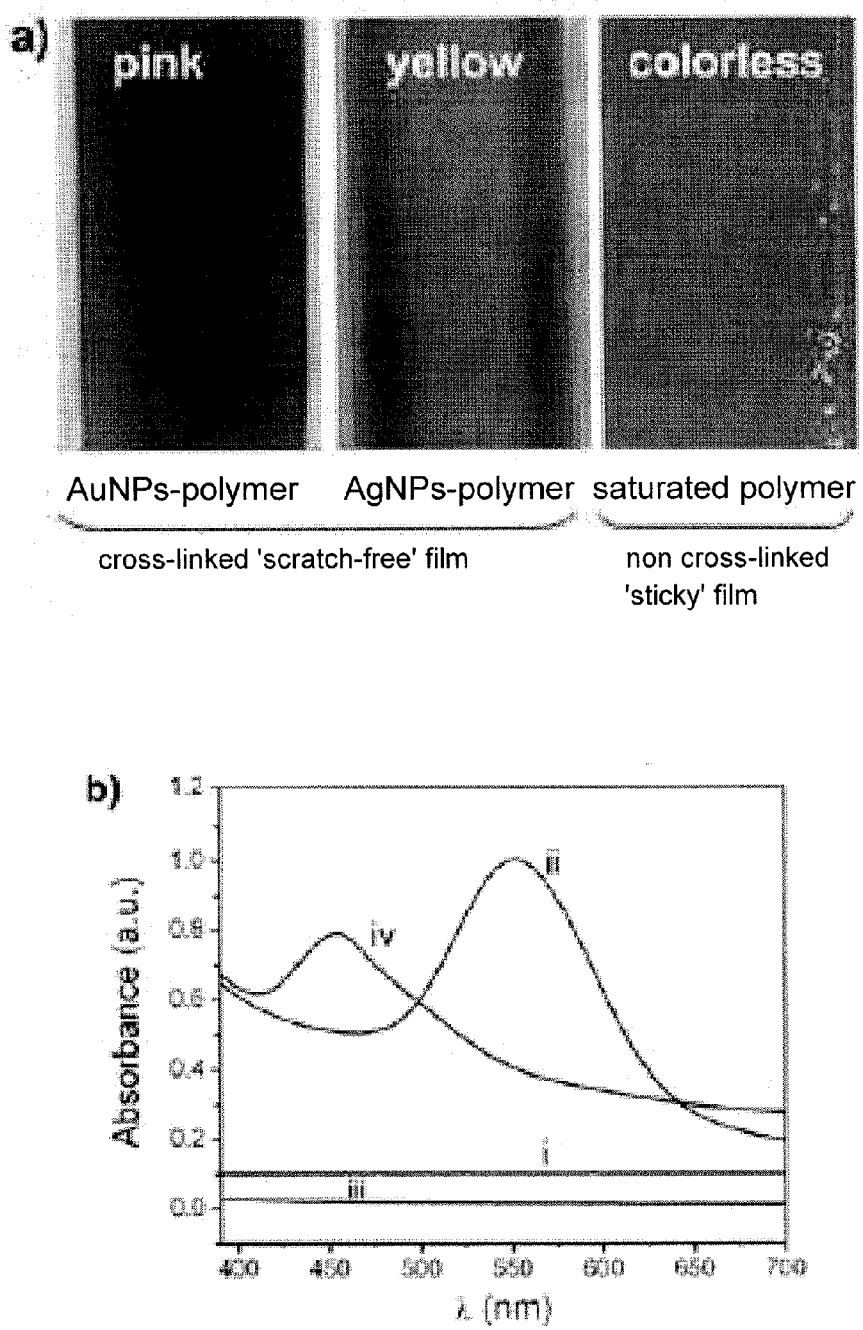
FIG. 2. (2*a*) Images of glass slides coated with PCA containing AuNPs (left), AgNPs (middle) and un-reduced metal salts (right); and (2*b*) absorption spectra of PCA after addition of chloroauric acid (i), and after AuNPs formed (ii). Similarly, after addition of silver benzoate (iii) and after AgNPs formed (iv).

Typically, metal salts were dissolved in a small amount of acetone, and added to the chloroform solution of PCA. Subsequently, the polymer-metal salts solution was coated on a glass slide. Evaporation of the solvent produced a sticky transparent colorless film. Upon exposure of those films to the air at ambient conditions (i.e., a natural drying process) for 10 hours, the sticky films converted into non-sticky, scratch-free transparent films. Visual changes were observed where the films turned pink and yellow in color. The color change indicated the formation of AuNPs and AgNPs, respectively, as shown in FIG. 2a. These transformations were also achieved by heating films at 60° C. for 30 minutes. The in situ-generated free radicals, created during the autoxidation, are responsible for the reduction of metal salts to generate MNPs. The stability and shelf life of NPs synthesized in this polymer are comparable to the NPs synthesized using a conventional process.

Example 2

In situ-prepared MNP-incorporated polymer films (e.g., alkyd resins) were characterized using different techniques including ultraviolet-visible spectrophotometry, transmission electron microscopy, scanning electron microscopy, energy-dispersive X-ray analysis, and X-ray photoelectron spectroscopy. The absorption spectrum of nanoparticles generated in oil was monitored as a function of time, as shown in the inset of FIG. 5e. It is clear from the spectra that absorbance at 450 nm increases as a function of time, and this peak appears for the AgNPs owing to the characteristic surface plasmon resonance effect originating from the quantum size of the AgNPs, which again confirms the formation of silver particles at nanoscale dimensions (Jin 2001). The absorbance maximum does not change over a long period, indicating that the silver particles are prevented from coagulating owing to stabilization of nanoparticles by fatty acids, which are essential constituents of the drying oil. Similarly, absorption spectra of in situ-synthesized AuNP-containing oil have shown a surface plasmon resonance peak at 540 nm, characteristic of AuNPs.

In order to quantify the ratio of $Ag^+$ to $Ag^0$, X-ray photoemission spectroscopy was performed. The Ag nanoparticles-oil medium is quite homogeneous so chemical composition does not change from surface to bulk. A solution-cast film of silver nanoparticles in oil was formed on Si(111) substrates and analyzed by XPS. A general scan spectrum of the film at room temperature showed the prominently presence of C 1s, O 1s, and Ag 3d core levels with no evidence of impurities. The film was sufficiently thick and, therefore, no signal was measured from the substrate (Si 2p core level).

The Ag 3d core level spectra were recorded from the Ag-oil film formed by the drop-coating technique. The Ag 3d spectrum could be resolved into a two spin-orbit pair (splitting ~6 eV) with a 3d5/2 binding energy (BE) of 368.1 and 369.3 eV (the core levels were aligned with respect to the adventitious C 1s BE of 285 eV). This BE corresponds to that of Ag(0) and Ag(I) state of silver and are in good agreement with the reported value. (Kumar 2003) The area occupied by peak is proportional to amount of silver present in different oxidation state in the samples. The ratio of area occupied of Ag(0) to Ag(I) peak is 7.5:1 indicate the relative ratio of metallic silver and silver ion present in the sample.

The absorption spectrums were recorded for metal salts that contained polymer films before and after the drying process, as shown in FIG. 2b. Absorption spectra of AuNPs that contained polymer showed a characteristic surface Plasmon resonance band at 555 nm, whereas such a peak was absent when recording absorption spectra immediately after addition of metal salts (before the drying process). This suggests the formation of AuNPs during the cross-linking process, as shown in FIG. 2b: (i) and (ii). Similarly, absorption spectra of in situ synthesized AgNPs in polymers show a peak at 460 nm. The peak is indicative of the AgNPs because of the characteristic surface Plasmon resonance effect originating from the quantum size effect of AgNPs (Jin 2001). In this instance, prior to the autoxidation (cross-linking) process, such an absorption band in UV was absent, as shown in FIG. 2b: (iii) and (iv). The formation of the absorption band suggests that MNPs are generated during the autoxidation process. The fact that the absorbance maximum does not change over a long period indicates that MNPs are prevented from coagulation because of stabilization of the NPs by the polymer.

FIG. 5e shows a representative transmission electron micrograph of AgNPs contained in the films (for more transmission electron micrographs of AgNPs and AuNPs. The average size of the AgNPs was found to be 12-14 nm; however, larger sizes in the 10-30 nm range were also occasionally observed (FIG. 5e). Similarly, the size range for AuNPs is 11-25 nm with a higher polydispersity. The AgNPs were further characterized using X-ray photoelectron spectroscopy.

Figure 3:
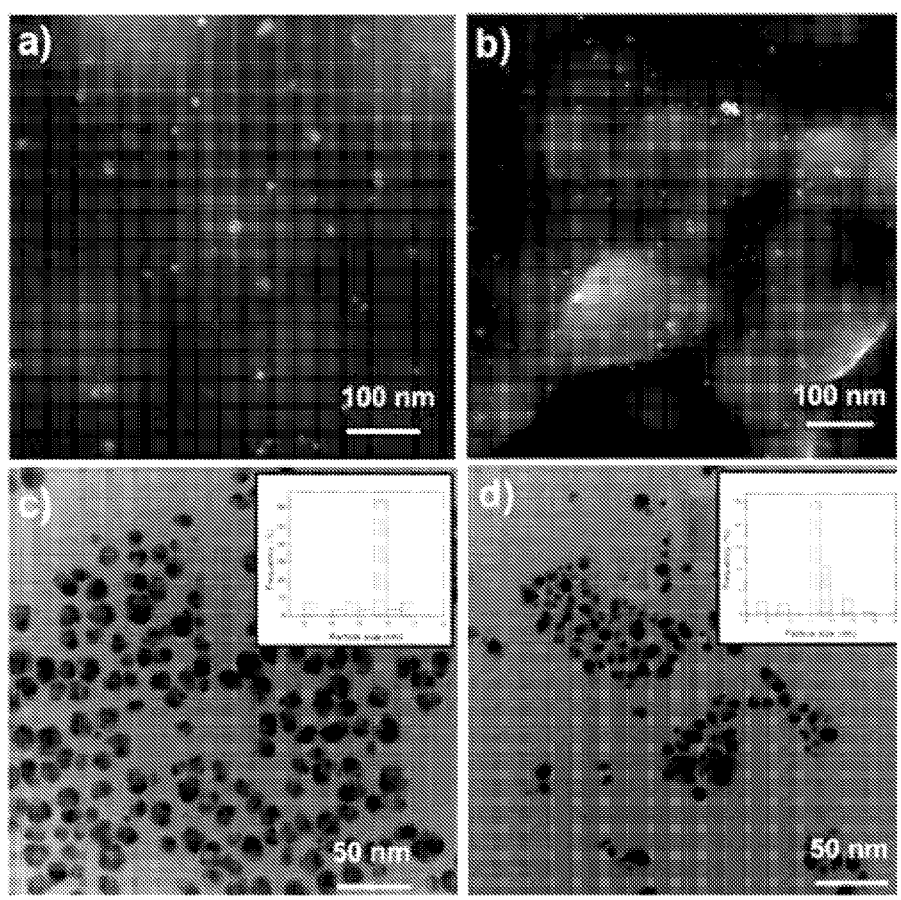
FIG. 3. SEM and TEM images of PCA. (3a) SEM images of PCA with AuNPs; (3b) SEM images of PCA with AgNPs; (3c) TEM images of PCA with AuNPs; and (3d) TEM images of PCA with AgNPs.

FIG. 3 shows SEM and TEM images of in situ synthesized AuNPs and AgNPs in PCA. The synthesized MNPs were nearly monodispersed with the average size of 18 nm for AuNPs, and 13 nm for AgNPs. Polydispersity of the particles were calculated from TEM data by plotting particle size distribution histogram Additionally, energy-dispersive X-ray analysis was used to confirm the presence of AgNP- and AuNP-embedded coatings. Thin films of AgNP- and AuNP-incorporated paints on silicon wafers were examined under a scanning electron microscope, where it was clear that the surfaces of the coatings were filled with metal nanoparticles. Spot analysis was carried out using energy-dispersive X-ray spectroscopy on the areas where particles were located, in the range of 4 keV, and characteristic peaks at 2.984 keV and 2.195 keV of silver and gold, respectively, were observed. In addition, the background materials showed representative peaks for carbon and oxygen. These results clearly suggest the presence of MNPs embedded in the drying oil-based paints.

Figure 4:
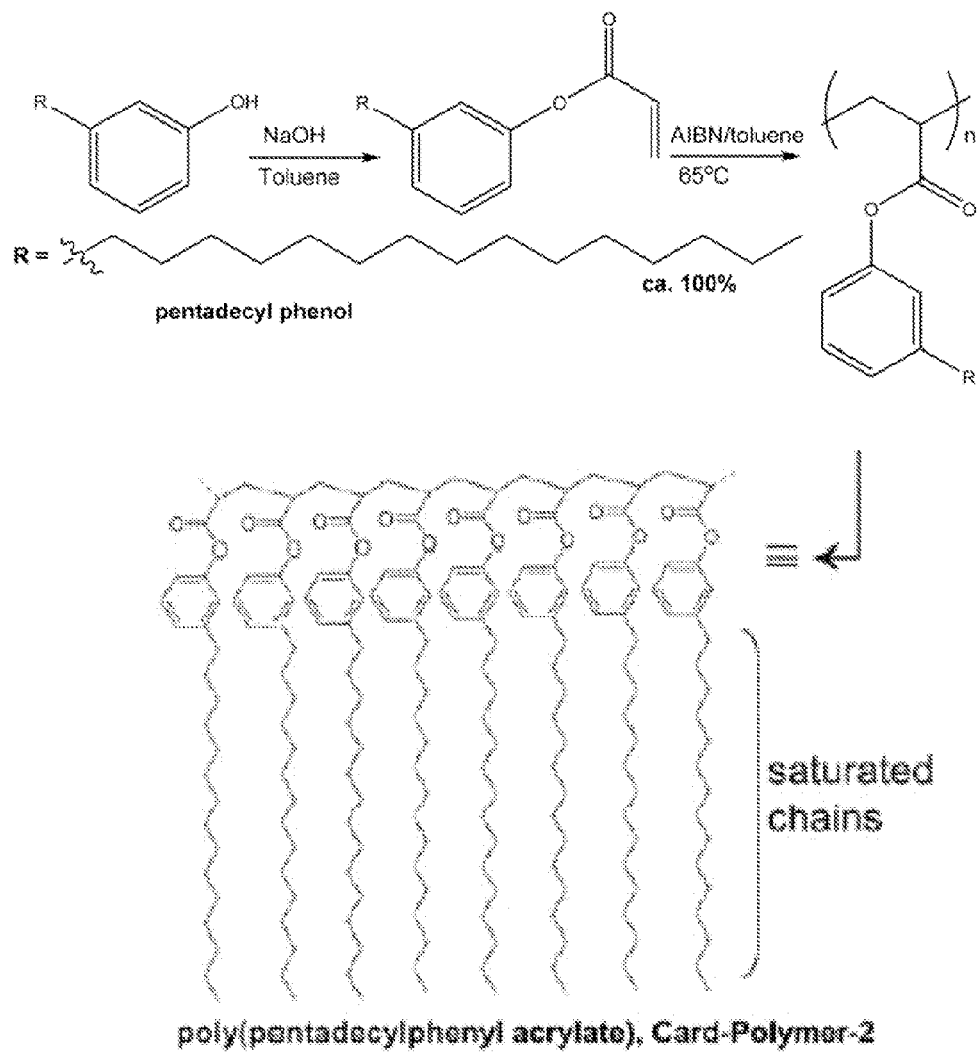
FIG. 4. Chemical structures of poly(pentadecylphenyl) acrylate (PPDA), which is a saturated analogue of PCA.

Free radicals generated during cross-linking of unsaturated chains of cardanol (autoxidation) are probably responsible for the reduction of metal salts to generate MNPs in situ. As a test, a saturated analogue, pentadecylphenyl acrylate (PDA) (shown in FIG. 1c) was synthesized. PDS was further polymerized similar to the cardanyl acrylate. The resulting polymer, poly(pentadecylphenyl) acrylate (PPDA) has only saturated chains. FIG. 4 shows chemical structures of PPDA, which is a saturated analogue of PCA. An acetone solution of metal salts was added to the PPDA in chloroform, and dropcasted on a glass slide akin to previous experiments. Evaporation of solvent produced sticky transparent film which remained as sticky transparent film even after seven days upon exposure to ambient conditions. The retention of the sticky character evidences the absence of the cross-linking process. This suggests that saturated chains lack the ability to cross-link. After seven days, these films were subjected to absorption spectroscopy. No surface plasmon resonance band corresponding to the MNPs appeared in the spectrum. This observation suggests that indeed in situ generated free radicals during cross-linking are responsible for the reduction of metal salt to produce MNPs in the polymer.

Free radicals generated during autoxidation are responsible for the reduction of metal salts. To prove this hypothesis, two sets of experiments were performed: one to enhance the reduction process by increasing the free radical generation and the rate of AuNP formation, and the other to completely prevent metal reduction using free radical scavengers.

It is well known that the addition of catalytic metals such as Co(II), Mn(III) and Fe(II) facilitates free radical formation and subsequently enhances the oxidative drying (lipid autoxidation) process (Van Gorkum 2005, Tang 2000). Silver benzoate and chloroauric acid were reduced separately by using oil in the presence of Fe(II) ions. The kinetics of nanoparticle formation was observed to be enhanced threefold (the $Ag^{+1}$ to $Ag^0$ reduction time decreased from 360 to 120 min, see FIG. 5f). The kinetics of nanoparticle formation was studied using absorbance spectra measurements of the in situ-synthesized AuNPs.

In the presence of a free radical formation-promoting catalyst, complete AgNPs formation was achieved in 2 hours. On the contrary, in the absence of catalyst 6 hours were needed for completion. In both cases, absorbance did not change over a long period of time (12 hours), indicating the particle formation has been completed and NPs are stable in the oil media. Rate enhancement of nanoparticle formation in the presence of a free radical initiator suggests that free radicals are indeed involved in the reduction process.

In the negative control experiments, the reduction process was carried out in the presence of free radical scavengers. Dimethylsulphoxide (DMSO) is known to act as a free radical scavenger, and is frequently used to prevent free radical-mediated processes (Ahmed 1998). DMSO (25% v/v) was mixed with the oil, and metal salts were then added and incubated for several months. Intriguingly, there was no nanoparticle formation, which was confirmed by absorption spectroscopy. Hence, these results unambiguously show that free radicals are indeed mostly responsible for the reduction of metal salts in the drying process.

In situ-synthesized MNPs are stable for several months without coagulation, owing to the passivation of MNPs with fatty acids and aldehydes. It is well documented that autoxidation ultimately leads to extensive fragmentation of the fatty-acid chains and generates a variety of biologically active products such as monoaldehydes, $\gamma$-ketoaldehydes, and 4-hydroxy-nonenal through free radical intermediates (Yin 2004, Esterbauer 1991). In addition, acids, aldehydes and free radicals are known to interact with MNPs to stabilize them (Vemula 2007, Nath 2004, Zhang 2003). Hence, the autoxidation reactions should produce fragments that bind to in situ-generated MNPs. In addition, the rigid cross-linked polymer (the product of the drying process of oil) also prevents nanoparticle aggregation, resulting in the production of nanoparticle-embedded homogeneous paints.

The AgNP-embedded drying oil is an excellent coating material and can be used to coat several kinds of surface such as wood, glass, polypropylene, poly(methyl methacrylate), polystyrene and building walls made of different materials. As MNPs are homogeneously dispersed in vegetable and cashew nut-based drying oil, the adhesion properties of AgNP- and AuNP-embedded paints were tested by coating them on different substrates such as glass and polymers, as shown in FIG. 6. To investigate the versatility of this process, several commercially available drying oil and paints were examined, such as bleached linseed oil, cold-pressed linseed oil, stand oil and Beckosol oils. In all cases, MNPs were successfully synthesized in situ by using the naturally occurring autoxidation as a tool during the drying process.

Silver is known to exhibit a broad spectrum of biocidal activity towards many bacteria, fungi and viruses (Russel 1994, Zachariadis 2004). Silver, in its uncharged state (i.e., an AgNP) is also found to possess antimicrobial properties. Although the mechanism of this action is still unresolved, it has been shown that AgNPs interact with the constituents of the outer membrane of bacteria, causing structural changes and degradation that eventually lead to the death of the bacterial cells (Sondi, 2004). AgNPs that are less than 15 nm in size are known to have efficient antibacterial activity (Morones 2005, Sudhir 1998). Hence, AgNP-embedded vegetable drying oils may be used as 'antibacterial paints' on different surfaces.

The bactericidal activity of in situ-synthesized AgNP-embedded vegetable drying oil was explored against both the airborne Gram-positive human pathogen *S. aureus* and its Gram-negative brethren *E. coli*. Surfaces were coated with the AgNP-embedded paint by either simple immersion of glass slides (2.5×7.5 cm) into the AgNP-embedded paint or spray coating of AgNP-embedded paint on glass slides followed by drying under air, which produced uniformly coated films. Bacterial colonies were grown on these slides, as discussed in the Methods section below.

Specifically, glass slides (2.5×7.5 cm) were coated with the AgNP-embedded paint by either simple immersion into AgNP-embedded paint or spray coating with the AgNP-embedded paint followed by drying in air. Both methods produced uniformly coated glass samples. The slides were left for one day or heated at 60° C. for 30 min to make sure that the drying process was complete, so that a scratch-free film was formed. Typically, a 100 μL suspension of *S. aureus* or *E. coli* in 0.1 M PBS (approximately $10^{11}$ cells $ml^{-1}$) was added to 20 ml of the yeast-dextrose broth in a 50 mL sterile centrifuge tube, followed by shaking at 200 rpm and 37° C. overnight (Innova 4200 Incubator Shaker, New Brunswick Scientific). The bacterial cells were collected by centrifugation at 6,000 rpm for 10 min (Sorvall RC-5B, DuPont Instruments), washed twice with PBS, and diluted to $5\times10^6$ cells $mL^{-1}$ for *S. aureus* and to $5\times10^7$ cells $ml^{-1}$ for *E. coli*. To mimic the aerosolized, airborne bacteria, we sprayed the bacterial suspensions in PBS onto slides at a rate of approximately 10 mL $min^{-1}$ in a fume hood. After drying for 2 min in air, the resultant slide was placed in a Petri dish and immediately covered with a layer of solid growth agar (1.5% agar in the yeast-dextrose broth, autoclaved, poured into a Petri dish, and allowed to gel at room temperature overnight). The Petri dish was sealed and incubated at 37° C. overnight, and the bacterial colonies grown on the slide surface were counted on a light box. The control experiments investigated the effects of a plain glass surface and paint without AgNPs; both types of bacterial solution were sprayed separately on commercially available glass slides and glass slides coated with oils without AgNPs, respectively.

The bacterial strains used were *S. aureus* and *E. coli*. The yeast-dextrose broth contained (per liter of deionized water): 10 g of peptone, 8 g of beef extract, 5 g of NaCl, 5 g of glucose, and 3 g of yeast extract. The PBS contained 8.2 g of NaCl and 1.2 g of $NaH_2PO_4.H_2O$ per liter of deionized water. The pH of the PBS solution was adjusted to 7.0 with 1N aqueous NaOH. Both solutions were autoclaved for 20 minutes before use.

After overnight incubation of the slides, the bacterial colonies were counted; images of the resulting glass slides are shown in FIG. 8. Each black dot corresponds to an individual bacterial colony. It can be seen in FIG. **8*a*** that the glass slide coated with AgNP-embedded paint killed almost all of the Gram-positive *S. aureus* bacteria compared with both the plain glass slide and the glass slide coated with paint without AgNPs.

In the present invention, the nanoparticles kill bacteria by rupturing their cell walls. As shown in FIG. 8, comparison of microbial growth on each of a glass slide, a glass slide with paint, and a glass slide with paint and nanoparticles, shows the antimicrobial effect of MNPs. The antimicrobial activity was determined to be 100%, because no bacterial colonies were observed under the microscope. The nanoparticles of the present invention also exhibit other significant antimicrobial activity, such as antiviral activity.

Figure 8:
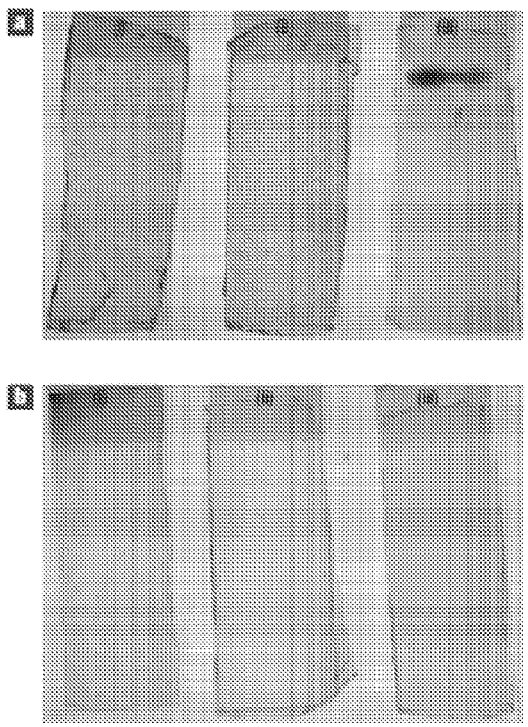
FIG. 8. Summary of the antibacterial properties of AgNP-containing paints. (8a) and (8b): photographs of commercially available blank glass slides without coating (i), glass slides coated with only drying-oil paint without nanoparticles (ii) and glass slides coated with AgNP-containing drying-oil paint (AgNP-embedded paint) (iii), onto which aqueous suspensions of approximately $5\times10^6$ cells $ml^{-1}$ of S. aureus cells (8a) and $5\times10^7$ cells $ml^{-1}$ of E. coli cells (8b) in PBS solution were sprayed, followed by drying in air for 5 min, covering with solid growth agar and incubating at 37° C. overnight. Each black dot corresponds to a bacterial colony grown from a single surviving bacterial cell.

Similarly, AgNP-embedded vegetable paints were equally active against the Gram-negative *E. coli* bacteria (FIG. 8b). In the case of *E. coli*, control experiments also showed that plain glass and glass coated with paint without AgNPs failed to kill the bacteria, suggesting that AgNPs are indeed responsible for the bactericidal activity. Previously, Morones et al. showed that AgNPs (where silver is present in the $Ag^0$ form) also contain micromolar concentrations of $Ag^+$ ions, and they have shown that $Ag^+$ and $Ag^0$ both contribute to the antibacterial activity (Morones 2005). To quantify the ratio of $Ag^0$ to $Ag^+$, X-ray photoemission spectroscopy was performed. The calculated ratio of $Ag^0$ to $Ag^+$ is 7.5:1. Hence, the silver ions and metallic silver both synergistically contribute to the enhanced antibacterial activity, in agreement with the earlier reports. The proficient bactericidal activity (see Table 1) of AgNP-embedded vegetable oil paints against both types of bacterium suggests the use of the present AgNP-incorporated paint formulations in other antimicrobial (e.g., antibacterial) coatings. All antibacterial tests were carried out in triplicate and were done a minimum of two different times to ensure reproducibility.

Table 1 shows bactericidal activity against airborne *S. aureus* and *E. coli* of glass slides coated with AgNPs embedded vegetable drying oil (AgNPs-paint). Bacterial suspensions ($5 \times 10^6$ cells/mL) in a PBS aqueous solutions were sprayed onto a surface of interest, dried in air for 5 min, placed in a Petri dish, covered with 1.5% solid growth agar, sealed, and incubated at 37° C. overnight, and then the colonies were counted.

TABLE 1

| Surface | bactericidal efficiency, % | |
|---|---|---|
| | S. aureus | E. coli |
| blank glass | 0 | 0 |
| glass + paint | 0 | 0 |
| glass + AgNPs-paint | "nearly total" | "nearly total" |

For the "blank glass," a commercially available glass slide (2.5 × 7.5 cm) was used as such without coating. For the "glass + paint," a glass slide was coated with vegetable drying oil (in this sample there are no AgNPs present). For the "glass + AgNPs-paint" a glass slide was coated with AgNPs embedded vegetable drying oils (AgNPs-paint). "Bactericidal efficiency" is defined as the number of bacterial colonies/cm² observed following cultivation on a coated slide divided by the number of bacterial colonies/cm² observed on the corresponding non-coated slide, times 100%. All experiments were carried out at least in triplicate.

Example 3

FIG. 9 shows the absorbance intensity at 450 nm increases as a function of time. This absorbance peak is due to the surface plasmon resonance of silver nanoparticles and is responsible for a characteristic yellow color. The plasmon absorbance intensity increase as a function of time and becomes saturated after 6 days (FIG. 9A), indicating the completion of the reaction. FIG. 9B shows the UV-visible spectra of Ag-oil and pure oil film formed at glass substrate. The peak at 450 nm (curve 2) is due to silver nanoparticles present in oil. However, pure oil (curve 1) does not show any unusual optical property. The color of the film does not change over a long period of time, which indicates that Ag nanoparticles are very stable and capped with oil molecules. This is an excellent coating material which can be used to coat any kind of substrate, ranging from polar to nonpolar substrates using this silver nanoparticles containing oil.

Figure 10:
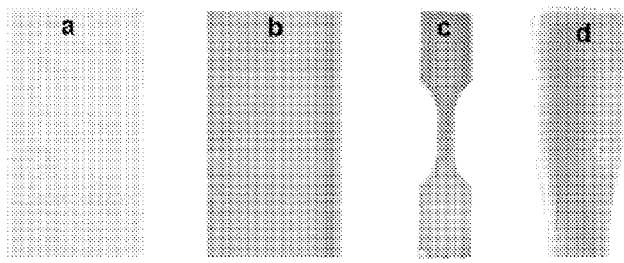
FIG. 10. Photograph of pure oil coated glass (10a), Ag-oil coated glass (10b), Polycarbonate (10c), Polymethylmethacrylate (10d).

FIG. 10 is a photograph of various materials such as pure oil coated glass (a), Ag-oil coated glass (b), Polycarbonate (c), Poly(methylmethacrylate) (d). These coatings are quite stable and indicate the excellent adhesion property of Ag-oil on both hydrophilic (e.g., ceramics, glass) and hydrophobic (e.g., polymers, etc.) substrates.

Example 4

Figure 11:
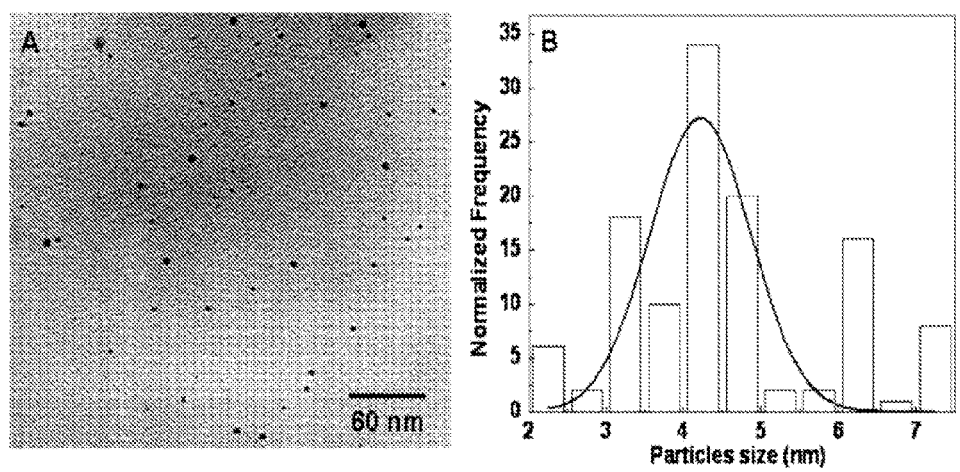
FIG. 11. (11a) TEM image of Ag-oil film on carbon coated copper grid film formed by solvent evaporation technique. (11b) Histogram of particles size measured from (11a).
Figure 12:
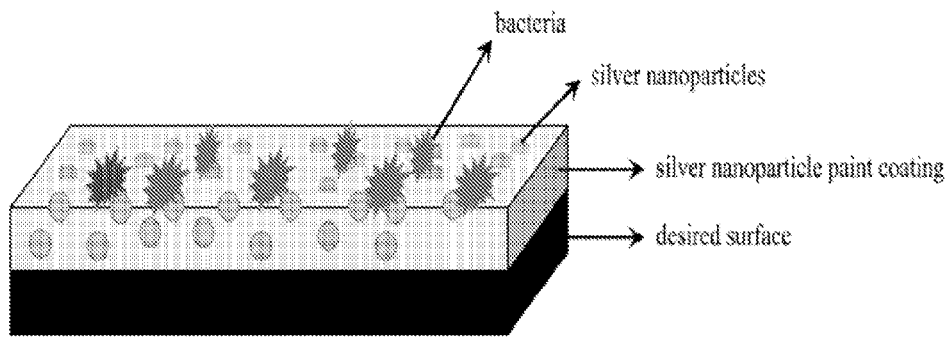
FIG. 12. NP-paint interaction with bacteria. Schematic representation of AgNPs-paint coated on desired surface which decontaminate the bacteria when it get in contact to the bacteria.

Drop-coated films of the Ag-alkyd resin were formed on carbon-coated copper grids by solvent evaporation technique for transmission electron microscopy (TEM) measurements. FIG. 11 shows representative TEM images of Ag-alkyd resin. It is clear from the TEM picture that the silver nanoparticles are discrete, quite uniform, and distributed all over the grid (FIG. 11A). FIG. 11B shows the histogram of the particle size distribution measured from particles in FIG. 11A and other similar micrographs. A Gaussian fit to the histogram yielded an average particle size of 4.4±0.2 nm.

Example 5

Antimicrobial/Antibacterial Activity

Bacteria and Media.

The bacterial strains employed were *Staphylococcus aureus* (ATCC 33807) and *Escherichia coli* (*E. coli* genetic stock center, CGSC4401). Yeast-dextrose broth contained (per liter of deionized water): 10 g of peptone, 8 g of beef extract, 5 g of NaCl, 5 g of glucose, and 3 g of yeast extract. Phosphate-buffered saline (PBS) contained 8.2 g of NaCl and 1.2 g of $NaH_2PO_4 \cdot H_2O$ per liter of deionized water. The pH of the PBS solution was adjusted to 7.0 with 1 N aqueous NaOH. Both solutions were autoclaved for 20 min prior to use.

Determination of Bactericidal Efficiency.

A 100-µl suspension of *S. aureus* or *E. coli* in 0.1 M PBS (approximately $10^{11}$ cells/mL) was added to 20 ml of the yeast-dextrose broth in a 50-ml sterile centrifuge tube, followed by shaking at 200 rpm and 37° C. overnight (Innova 4200 Incubator Shaker, New Brunswick Scientific). The bacterial cells were harvested by centrifugation at 6,000 rpm for 10 min (Sorvall RC-5B, DuPont Instruments), washed twice with PBS, and diluted to $5 \times 10^6$ cells/ml for *S. aureus* and to $5 \times 10^7$ cells/ml for *E. coli*. The bacterial suspensions in PBS were sprayed onto slides at a rate of approximately 10 ml/min in a fume hood. After a 2-min drying under air, the resultant slide was placed in a Petri dish and immediately covered with a layer of solid growth agar (1.5% agar in the yeast-dextrose broth, autoclaved, poured into a Petri dish, and allowed to gel at r.t. overnight). The Petri dish was sealed and incubated at 37° C. overnight, and the bacterial colonies grown on the slide surface were counted on a light box.

The samples were tested against gram positive (*Staphylococcus aureus*) and gram negative (*E. coli*) bacteria. Triplicate was done for every case. The plane glass slide was used as a control. 100% antibacterial efficiency means there was no colony in the entire slide after 24 h incubation. 0% antibacterial efficiency means there was no statistically significant difference compared to the control slide as shown in Table 2.

TABLE 2

| Sample | Staphylococcus aureus (gram positive) | E. coli (gram negative) |
|---|---|---|
| Coated slide | 100% | 100% |
| Uncoated slide | 0% | 0% |

Example 6

The present invention relates to a simple shaking process either by complexing metal ion with drying oil molecules at the nonpolar solvent (paint thinner)-water interface or by dissolving a organometallic complex in oil medium and then in situ formation nanoparticles in the organic phase. The critical goal of the present invention is to provide an improved process for the synthesis of metal nanoparticles such as gold, silver, platinum, nickel, copper, ruthenium and palladium directly in coating materials for various applications.

Figure 13:
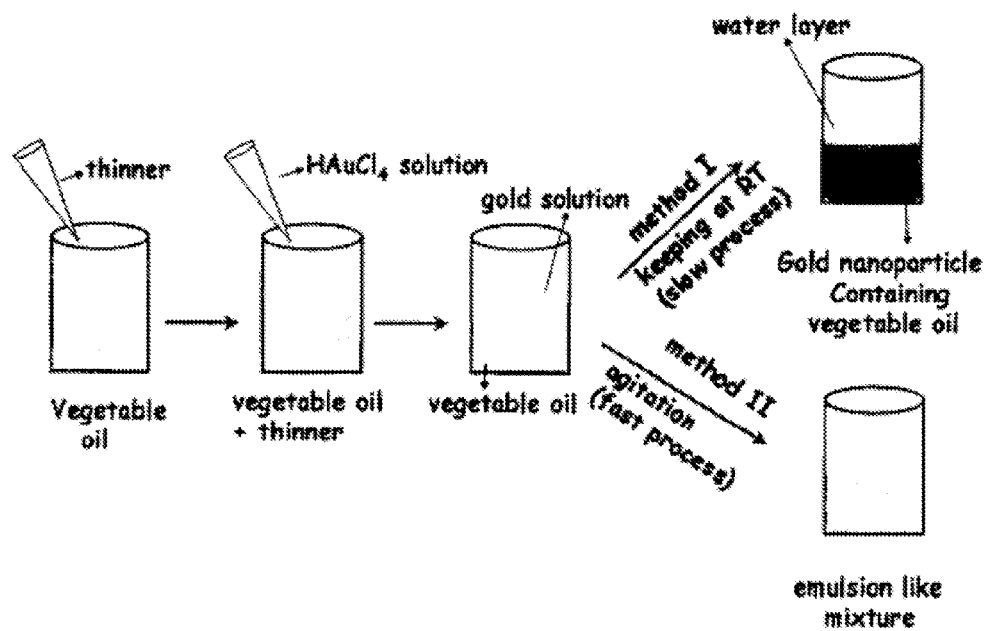
FIG. 13. Schematic diagram for the synthesis of gold nanoparticles using vegetable oil.

Another object is to make metal nanoparticles coated with hydrophobic groups in various organic solvents, which can be used for commercial purpose. Accordingly, the present invention provides a process for the preparation of nanoparticles dispersion which comprises of mixing an aqueous solution of metal ion with a solution of drying oil in an organic solvent under agitation (see FIG. 13).

Example 7

These nanoparticles have been characterized by various techniques such as transmission electron microscopy (TEM), UV-visible spectroscopy etc. Observation of the TEM image showed that gold nanoparticles were obtained using this protocol. The gold nanoparticles are discrete, quite uniform and stable.

Average particle size was calculated by combining the data from the TEM images The gold nanoparticles were with the size of 10 to 50 nm, major portion of the nanoparticles are in the size dimension of ~12 nm. These particles are dispersed in vegetable oil paints therefore thin film of this metal nanoparticles dispersion can be obtained on any substrate. To demonstrate the concept, the paint-containing nanoparticles were coated onto various substrates such as ceramic, glass or silicon wafer, and polymers. It was clear that coated glass and polymer look ruby red in color and the coating was quite uniform, indicating that this dispersion adhere very well on these substrates.

This method could be equally and easily applied to the generation of art work and designs in RUBY RED, in place of traditional golden yellow art work in ceramic-ware and crockery industry. Dip coated film of gold nanoparticles-oil film was formed on glass and analyzed by UV-visible spectrometer as a function of temperature. UV-Visible spectra were taken of film at room temperature and after heating at 200 and 400° C. for 1 hr at each temperature. The absorbance at 560 nm corresponds to the surface plasmon resonance, which was originally at 560 nm, shifts to the higher wavelength region with temperature. This shift in surface plasmon of resonance is due to aggregation of the particles in the film. It is likely that above 200° C., desorption occur of polymerized oil from the gold nanoparticles and this leads to sintering of the particles. Aggregation of nanoparticles was also studied using atomic force microscope. Dip coated film of gold nanoparticles-oil dispersion was made on silicon wafer and scan in tapping mode using Nanoscope III instrument.

The AFM image was obtained for the dip coated film of gold oil dispersion on silicon wafer. The line profile was also obtained. The AFM image was obtained for the same film after heating at 400° C. for one hour and corresponding line profile. It is clear from the line profile that gold film is quite uniform and individual gold nanoparticles are not seen in the image. It indicates that particles are covered with polymers form due to oxidation of oil. On annealing the film become very rough due to the aggregation of gold nanoparticles and individual aggregates can be seen in AFM image which is in good agreement with the UV-visible studies.

This nanoparticle synthesis process was also simplified and organometallic compounds (e.g., silver benzoate) were used as a precursor for the synthesis of metal nanoparticles directly in oil. In this process, organometallic compounds were dissolved directly in oil phase, which got decomposed during drying process of oil and form nanoparticles.

Example 8

This example illustrates the synthesis of gold nanoparticles with drying oil at the hexanewater interface and then the phase transfer of gold nanoparticles in the organic phase. In a typical experiment, 30 mL of a $10^{-2}$ M solution of gold chloride, (Sigma chemicals, used as-received) in water was added to 30 mL hexane containing 3 gm of oil (Miniwax, Antique oil finish, used as-received). This biphasic solution was kept in dark for 24 hour under agitation for the formation of nanoparticles in organic phase.

Example 9

This example illustrates the synthesis of silver nanoparticles with drying oil at the hexane-water interface and then the phase transfer of silver nano-particles in the organic phase. In a typical experiment, 30 mL of a $10^{-2}$ M solution of silver nitrate, (Sigma chemicals, used as-received) in water was added to 30 mL hexane containing 3 gm of oil. (Miniwax, Antique oil finish, used as received). This biphasic solution was kept in dark for 24 hour under agitation for the formation of nanoparticles in organic phase.

Example 10

This example illustrates the synthesis of copper nanoparticles with drying oil at the hexane-water interface and then the phase transfer of copper nanoparticles in the organic phase. In a typical experiment, 30 mL of a $10^{-2}$ M solution of copper sulfate, (Sigma chemicals, used as-received) in water was added to 30 mL hexane containing 3 gm of oil (Miniwax, Antique oil finish, used as-received). This biphasic solution was kept in dark for 24 hour under agitation for the formation of nanoparticles in organic phase.

Example 11

This example illustrates the synthesis of silver nanoparticles with drying oil. In a typical experiment 0.034 gm of silver benzoate was dissolved in 75 mL of toluene. 4.8 gm of alkyd resin was mixed in the solution and kept it in dark for 12 hours. The oil become yellow after 12 hours due to formation of silver nanoparticles.

Methods

Nanoparticle Synthesis in Oil.

In one experiment, 0.034 g silver benzoate was dissolved in 4.8 g alkyd paint (all experiments were done with Miniwax, Antique oil finish unless otherwise specified, which was used as-received) and was mixed to form a homogeneous solution and kept at room temperature. Similarly, for the synthesis of AuNPs, 0.136 g of $HAuCl_4$ was added to 20 mL of drying oil and was mixed with a glass rod to form a green colored oil, which remained as a gold salt for three weeks. For the MNP synthesis, oil containing metal salts was coated on the glass surfaces and left to dry in air, which caused autoxidation that subsequently led to the formation of MNP-embedded drying-oil scratch-free coatings.

Poly(Cardanyl Acrylate) Synthesis.

Cardanol was obtained by double vacuum distillation of cashew nut shell liquid at 3-4 mm Hg; the fraction distilled at 230-235° C. was collected. The monomer, cardanyl acrylate and poly(cardanyl acrylate) were synthesized as reported earlier (John 1992, John 1993).

Nanoparticle Synthesis in Synthetic Polymer.

Metal salts (silver benzoate or chloroauric acid) were dissolved in acetone, and added to a chloroform solution of poly(cardanyl acrylate). The mixture was coated on the glass slides and left in air to dry, which caused autoxidation and the subsequent formation of MNP-embedded polymeric scratch-free coatings.

Transmission Electron Microscopy.

Transmission electron microscopy data were recorded using a Zeiss EM-902 transmission electron microscope (80 kV). Nanoparticle-embedded oil was placed directly on a 10×10 mm plastic sheet, and after drying at 60° C. for 4 h, it was cut using a microtome to obtain 100-nm-thick slices, which were placed directly on a Cu grid and examined under a transmission electron microscope.

Scanning Electron Microscopy and Energy-Dispersive X-Ray Spectroscopy.

A small amount of nanoparticle-embedded oil was placed on a silicon wafer to form a thin layer; the silicon wafer was dried at ambient conditions for 24 h, and was directly examined using a field-emission scanning electron microscope (JEOL-6330F) operated at 5 kV. Energy-dispersive X-ray data were also collected from the same sample at 15 kV using a Prism 2000 Si(Li) X-Ray detector (Princeton Gamma-Tech) coupled with a Zeiss DSM-940 microscope.

Ultraviolet-Visible and X-Ray Photoelectron Spectroscopy.

Nanoparticle-embedded oil was placed on glass slides and dried to form thin films, which were examined directly with a Perkin Elmer Lamda-950 spectrophotometer operated at a resolution of 2 nm and a PHI-5400 instrument with a 200 W Mg K$\alpha$ probe beam. The spectrometer was configured to operate at high resolution with a pass energy of 20 eV.

Characterization of poly(cardanyl acrylate).

The number- and weight-average molecular weights of polymer was determined by a Waters Associates model 440 gel permeation chromatograph having μ-styragel column of pore size $10^5$, $10^4$, and $10^3$ Å connected in series and UV detector. Chloroform was used as the mobile phase. The instrument was calibrated using standard samples of polystyrene. The number- and weight average molecular weights of the polymer before cross-linking as determined by GPC were 3000 and 11,000 respectively.

DSC:

DSC was recorded using a Mettler TA 3000 system in air at a heating rate of 5° C./min from 30 to 200° C. DSC curve of poly(cardanyl acrylate) shows an exotherm at 80-185° C. and a peak maxima of 132.1° C., indicating a polymerization reaction. This might be due to cross-linking of polymer.

IR:

The C—H stretching vibrations of the unsaturated part of the side chain of the monomer CA was observed at 3020 $cm^{-1}$, which is characteristic of disubstituted olefinic system. This is further clarified from the observation that this peak is absent in saturated analog of cardanyl acrylate where the side chain has no double bond. The double bond of acrylic moiety was observed at 1658 $cm^{-1}$, and in the poly(cardanyl acrylate), the peat at 1658 $cm^{-1}$ was not observed, due to the conversion of acrylic C=C to C—C, where as the peak at 3020 $cm^{-1}$ did not change. This is clearly indicating that the side chain of monomer with its double bonds remains intact in the polymer and polymerization takes place only through the acrylate double bonds.

$^1$H-NMR:

In the $^1$H-NMR of cardanyl acrylate monomer the peaks were assigned for different protons (δ, ppm): 0.8 (t, $CH_3$), 1.11-1.5 [m, $(CH_2)$], 1.7-2.2 (m, —$CH_2$—CH=CH—), 2.2-2.8 (m, —$CH_2$—Ar), 5.2-5.5 (t, $CH_2$=CH—, —CH=CH—), 5.7-6.1 (m, =$CH_2$), 6.3-6.6 (m, —CH=), 6.8-7.3 (m, aromatic). In the NMR spectrum of poly(cardanyl acrylate) the peak at δ=5.7-6.6 (acrylic) is not present due to polymerization through acrylate moiety and the peak at δ=5.2-5.5 for the double bonds in the side chain of the monomer remains intact after the polymerization reaction, which also supports the IR data.

In summary, a renewable resources based monomer (cardanol from CNSL) was used to prepare a biobased polymer. In situ synthesis of MNPs has been achieved with this polymer without using any external reducing and stabilizing agents. In situ-generated free radicals during oxidative drying of cardanol unsaturated chains were used as a tool for MNPs synthesis, and was confirmed by synthesizing saturated analogue polymer which failed to generate MNPs. MNP-embedded polymers films were stable at ambient conditions for a longer period. The preparation of organic-inorganic hybrid materials may have applications in developing materials with tunable optical, electrical, and catalytic properties. AgNPs embedded biobased polymers have potential antibacterial activity.

BIBLIOGRAPHY

Abyaneh, et al., *J. Phys. D: Appl. Phys.* 2007, 40, 3771-3779

Ahmed-Choudhury, et al., *Toxicol. Appl. Pharmacol.* 152, 270-275 (1998)

Alt, et al., *Biomaterials* 25, 4383 (2004)

Anastas & Williamson, Green Chemistry: Frontiers in Benign Chemical Syntheses and Processes (Oxford Univ. Press, Oxford, 1998)

Aymonier, et al., *Chem. Commun.* 3018-3019 (2002)

Baschong, et al. *J. Electron Microsc. Tech.,* 1990, 14, 313.

Berger, et al., *Antimicrob. Agents Chemother.* 9, 357-358 (1976)

Bieleman, Additives for Coatings (Wiley-VCH, Weinheim, 2000)

Biermann, et al., *Angew. Chem. Int. Ed.* 2000, 39, 2206-2224

Bishop, et al., *Gold Bull.* 35 (3), 89, 2002.

Black, *J. Am. Chem. Soc.* 100, 527-535 (1978)

Bohannon, *Science* 309, 376-377 (2005)

Bond, et al. *Catal. Rev. Sci. Eng.* 41, 319 (1999)

Brust, et al. *J. Chemn. Soc. Commun.,* 1994, 801

Chou, et al. *Polym. Adv. Technol.* 16, 600-607 (2005)

Colvin, et al., *Nature* 1994, 370, 354

Corma, et al., *Chem. Rev.* 2007, 107, 2411-2502

Crisp, et al., *Nano Lett.* 3, 173-177 (2003)

Dai, et al., *Nano Lett.* 2, 497-501 (2002)

Daniel, et al., *Chem. Rev.* 2004, 104, 293-346

Daniel (ed.), Bailey's Industrial Oil and Fat Products (Wiley, NY, 1964)

Dowling, et al. *Surf Coat. Technol.* 163, 637-640 (2003)

Elghanian, et al., *Science,* 1997, 277, 1078

Esterbauer, et al., *Free Radic. Biol. Med.* 11, 81-128 (1991)

Fustin, et al., *Langmuir* 2006, 22, 6690-6695

Gogoi, et al., *Langmuir* 22, 9322-9328 (2006)

Goldemberg, *Science* 2007, 315, 808-810

Haldar, et al., *Proc. Natl. Acad. Sci. USA* 103, 17667-17671 (2006)

Hellmann, A. Polymer Films with Embedded Metal Nanoparticles (Springer, NY, 2002)
Hoffman, et al. *J. Phys. Chem.*, 1992, 96, 5546.
Hotchkiss, et al., *Chem. Mater.* 2007, 19, 6-13
Iwakoshi, et al., Proceedings of the International Conference 'Gold2003: New Industrial Applications for Gold', Vancouver, Canada, Sep. 28-Oct. 1, 2003
Jiang, et al., *J. Appl. Polym. Sci.* 93, 1411-1422 (2004)
Jin, et al., *Science* 2001, 294, 1901-1903
John, et al., *Makromol. Chem., Rapid. Commun.* 1992, 13, 255
John, et al., *J. Polym. Sci. Part A: Polym. Chem.* 1993, 31, 1069-1073
John, et al., *Adv. Mater.* 2001, 13, 715-718
John, et al., *Chem. Eur. J.* 2002, 8, 5494-5500
John, et al., *J. Am. Chem. Soc.* 2004, 126, 15012-15013
John, et al., *Angew. Chem. Int. Ed.* 2006, 45, 4772-4776
John, et al., *Soft Matter* 2006, 2, 909-914
Kenawy, et al., *Biomacromolecules* 8, 1359-1384 (2007)
Klabunde, et al. *Nanoscale materials in chemistry* (2001)
Klaus, et al., *Proc. Natl. Acad. Sci. USA* 96, 13611-13614 (1999)
Kumar, A. et al. *J. Colloid Interface Sci.* 264, 396-401 (2003)
Lansdown, *J. Wound Care.* 11, 125-130 (2002)
Lewis, et al., *Trends Biotechnol.* 23, 343-348 (2005)
Lichtenthaler, *Acc. Chem. Res.* 2002, 35, 728-737
Liu, et al., *Anal. Chem.* 2007, 79, 2221-2229
Lu, et al., *Lett.* 5, 5-9 (2005)
Mallia, et al., *Angew. Chem. Int. Ed.* 2007, 46, 3269-3274
Metzger, et al., *Appl. Microbiol. Biotechnol.* 71, 13-22 (2006)
Morones, et al., *Nanotechnology* 16, 2346-2353 (2005)
Morones, et al., *Langmuir* 2007, 23, 8180-8186
Naik, et al., *Nature Mater.* 1, 169-172 (2002)
Nath, et al., *Ind. J. Chem. A* 43, 1147-1151 (2004)
Okitsu, et al., Maeda, *Chem. Mater.* 1996, 8, 315-317
Okitsu, et al., *J. Phys. Chem. B* 1997, 101, 5470-5472
Pagliaro, et al., *Angew. Chem. Int. Ed.* 2007, 46, 4434-4440
Podsiadlo, et al. *Langmuir* 21, 11915-11921 (2005)
Prashant, et al. *Biotech & Bioeng* (2005) 90, 59
Raveendran, et al., *J. Am. Chem. Soc.* 125, 13940-13941 (2003)
Reich & Stivala, Autoxidation of Hydrocarbons and Polyolefins (Marcel Dekker, NY, 1969)
Rostrup-Nielsen, *Science* 2005, 308, 1421-1422
Russel, et al., *Prog. Med. Chem.* 31, 351-370 (1994)
Sambhy, et al., *J. Am. Chem. Soc.* 128, 9798-9808 (2006)
Shan, et al., *Macromolecules* 2003, 36, 4526-4533
Shan, et al., *Macromolecules* 2005, 38, 2918-2926
Shankar, et al. *Chem. Mater.* 2005, 17, 566.
Shimmin, et al., *Langmuir* 2004, 20, 5613-5620
Shipway, et al. *Chem. Mater.* 1999, 11, 13-15
Sondi, et al., *J. Colloid Interface Sci.* 275, 177-182 (2004)
Sudhir, Langmuir 14, 1021-1025 (1998)
Tang, et al., *Biochem. J.* 352, 27-36 (2000)
Taton, et al. *Science* 2000, 289, 1757.
Tyman, *Chem. Soc. Rev.* 1979, 8, 499-537
Van Gorkum, et al., *Coordination Chem. Rev.* 249, 1709-1728 (2005)
Vemula, et al., *Chem. Commun.* 2006, 2218-2220
Vemula, et al., *J. Am. Chem. Soc.* 2006, 128, 8932-8938
Vemula, et al., *Chem. Mater.* 2007, 19, 138-140
Wang, et al. *Chem. Mater.* 2006, 18, 1988-1994
Williams, et al., *Crit. Rev. Biocompat.* 5, 221-243 (1989)
Yin, et al., *J. Biol. Chem.* 279, 3766-3776 (2004)
Yin, et al., *Antioxid. Redox Signal.* 7, 170-184 (2005)
Zachariadis, et al., *Eur. J. Inorg. Chem.* 2004, 1420-1426 (2004)
Zhang, et al., *J. Am. Chem. Soc.* 125, 7959-7963 (2003)
Zhang, et al., *Angew. Chem. Int. Ed.* 2006, 45, 1116-1119
Zheng, et al., *Langmuir* 2004, 20, 4226-4235

All references cited and/or discussed in this specification are incorporated herein by reference in their entireties and to the same extent as if each reference was individually incorporated by reference.

We claim:

1. A method for preparing metal nanoparticles in a drying oil, comprising the steps of:
   (a) mixing a solution comprising metal ions with a solution comprising a drying oil in the presence of an organic solvent or
   mixing a solution comprising an organometallic compound with a solution comprising a drying oil in the presence of an organic solvent;
   (b) agitating the mixture for a period of 12 to 24 hours; and
   (c) polymerizing the drying oil by autoxidation to form metal nanoparticles in the polymerized oil,
   wherein the method does not include an external reducing agent.

2. The method of claim 1, wherein the metal nanoparticle are hydrophobic.

3. The method of claim 1, wherein the metal ions are selected from gold, silver, nickel, platinum, palladium, cadmium, zinc, copper, and combinations thereof.

4. The method of claim 1, wherein the drying oil is selected from cashew nut shell liquid, linoleic acid, poppy oil, soyabean oil, urushi oil, linseed oil, sunflower oil, tung oil, alkyd resins, and combinations thereof.

5. The method of claim 1, wherein step (a) occurs in the presence of an organic solvent selected from n-hexane, chloroform, heptane, octane, petroleum ether, benzene, toluene, turpentine, and combinations thereof.

6. The method of claim 1, wherein step (a) occurs in the presence of an organometallic compound selected from silver benzoate, metal acetyl acetonates, metal carbonyls, nonpolar metal salts, and combinations thereof.

7. The method of claim 6, wherein the organometallic compound is selected from iron acetyl acetonate, platinum acetyl acetonate, nickel acetyl acetonate, cobalt acetyl acetonate, cobalt acetate, iron petacarbonyl, and combinations thereof.

* * * * *